United States Patent
Levin et al.

(10) Patent No.: US 9,017,681 B2
(45) Date of Patent: Apr. 28, 2015

(54) ADENYLYL CYCLASES AS NOVEL TARGETS FOR ANTIBACTRIAL INTERVENTIONS

(75) Inventors: Lonny Levin, New York, NY (US);
Jochen Buck, Old Greenwich, CT (US);
Leo Brizuela, Hamilton, MA (US);
Michael Pinnisi, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 80 days.

(21) Appl. No.: 12/523,011

(22) PCT Filed: Jan. 11, 2008

(86) PCT No.: PCT/US2008/000448
§ 371 (c)(1),
(2), (4) Date: Feb. 3, 2010

(87) PCT Pub. No.: WO2008/121171
PCT Pub. Date: Oct. 9, 2008

(65) Prior Publication Data
US 2010/0168203 A1    Jul. 1, 2010

Related U.S. Application Data

(60) Provisional application No. 60/880,277, filed on Jan. 12, 2007.

(51) Int. Cl.
*A61K 31/122*     (2006.01)
*A61K 31/415*     (2006.01)

(52) U.S. Cl.
CPC ........ *A61K 31/415* (2013.01); *G01N 2333/988* (2013.01); *G01N 2500/00* (2013.01)

(58) Field of Classification Search
CPC ..................... A61K 31/122; A61K 2300/00
USPC ....................................................... 424/146.1
See application file for complete search history.

(56) References Cited

U.S. PATENT DOCUMENTS 4,061,746 A * 12/1977 Blohm et al. .................. 514/183
4,344,952 A *  8/1982 Hernestam et al. ........... 514/317
(Continued)

FOREIGN PATENT DOCUMENTS

WO        01/85773     * 11/2001     ............. C07K 14/28
WO     2003/037370     *  5/2003
(Continued)

OTHER PUBLICATIONS

Antimicrobial Activities, Gazi Universitesi Eczacilik Fakultes Ankara, 1992, vol. 9(1), pp. 47-57.*
(Continued)

*Primary Examiner* — Gary Nickol
*Assistant Examiner* — Ginny Porter
(74) *Attorney, Agent, or Firm* — Kenyon & Kenyon LLP

(57) ABSTRACT

The present invention relates to a method of preventing or treating a disease caused by bacterial infection by administering an effective amount of a modulator of bacterial adenylyl cyclase. The invention also provides pharmaceutical compositions useful for preventing or treating a disease, with the compositions containing a therapeutically effective amount of a modulator of bacterial adenylyl cyclase. The invention also provides screening methods for identifying selective modulators of bacterial adenylyl cyclase that do not substantially modulate adenylyl cyclase of the subject. The invention also provides methods for culturing bacterial pathogens and methods for inducing the pathogenic state in vitro.

51 Claims, 2 Drawing Sheets

(56) References Cited

U.S. PATENT DOCUMENTS

Figure 1:
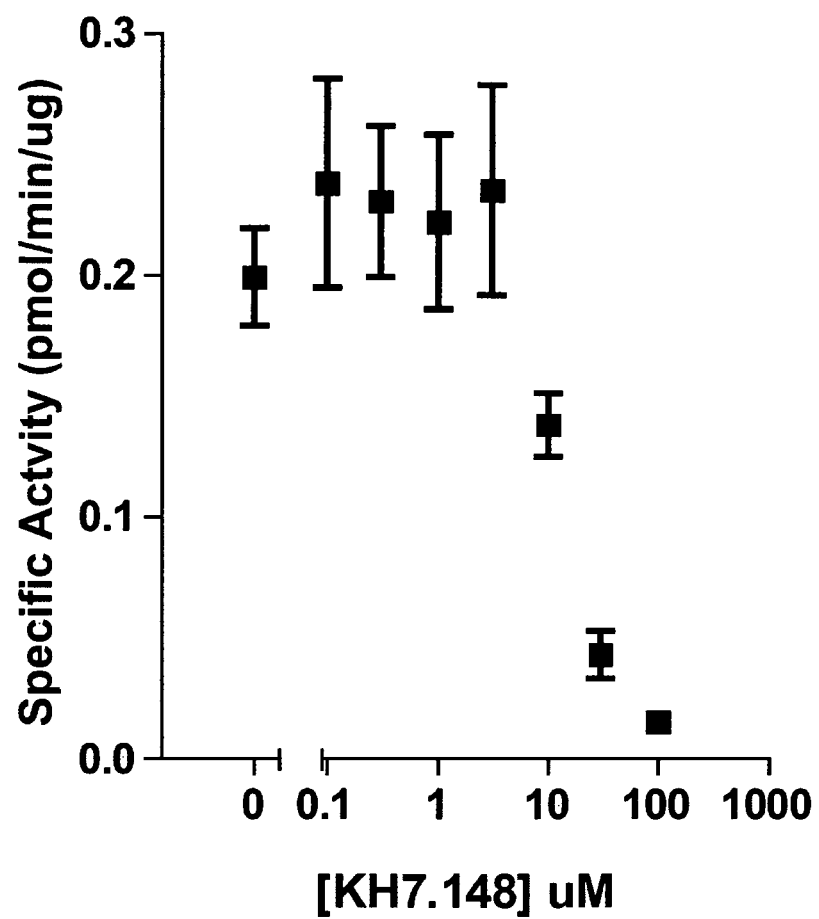

| | | | | |
|---|---|---|---|---|
| 4,724,223 | A * | 2/1988 | Ditchek | 438/571 |
| 5,405,944 | A * | 4/1995 | Suzuki et al. | 536/5 |
| 5,602,110 | A * | 2/1997 | Drumm et al. | 514/47 |
| 6,132,957 | A * | 10/2000 | Johnson et al. | 435/4 |
| 6,218,594 | B1 * | 4/2001 | Tsibris et al. | 800/3 |
| 6,309,648 | B1 * | 10/2001 | Betsou et al. | 424/203.1 |
| 6,544,768 | B1 * | 4/2003 | Buck et al. | 435/232 |
| 6,546,768 | B1 * | 4/2003 | Burghoff et al. | 70/252 |
| 6,559,176 | B1 * | 5/2003 | Bassler et al. | 514/408 |
| 6,994,854 | B1 * | 2/2006 | Betsou et al. | 424/150.1 |
| 7,438,909 | B2 * | 10/2008 | Morrow et al. | 424/142.1 |
| 7,442,373 | B2 * | 10/2008 | Morrow et al. | 424/130.1 |
| 7,449,459 | B2 * | 11/2008 | Buchmann et al. | 514/232.8 |
| 7,462,472 | B2 * | 12/2008 | Tang et al. | 435/183 |
| 7,786,139 | B2 * | 8/2010 | Bergmann et al. | 514/311 |
| 7,906,123 | B1 * | 3/2011 | Leclerc et al. | 424/234.1 |
| 7,947,268 | B2 * | 5/2011 | Baillie | 424/93.2 |
| 8,461,128 | B2 * | 6/2013 | Tan et al. | 514/46 |
| 2001/0041333 | A1 | 11/2001 | Short et al. | |
| 2002/0032228 | A1 * | 3/2002 | Peterson et al. | 514/396 |
| 2002/0169140 | A1 * | 11/2002 | Prendergast | 514/45 |
| 2002/0188016 | A9 * | 12/2002 | Peterson et al. | 514/396 |
| 2002/0197272 | A1 * | 12/2002 | Galloway et al. | 424/190.1 |
| 2003/0023032 | A1 * | 1/2003 | Bassler et al. | 530/350 |
| 2003/0108556 | A1 * | 6/2003 | Mekalanos et al. | 424/184.1 |
| 2003/0157644 | A1 * | 8/2003 | Iyengar et al. | 435/69.1 |
| 2004/0006122 | A1 | 1/2004 | Fensome et al. | |
| 2004/0009927 | A1 * | 1/2004 | Romeo et al. | 514/23 |
| 2004/0180829 | A1 * | 9/2004 | Bassler et al. | 514/12 |
| 2005/0271679 | A1 * | 12/2005 | Dadaglio et al. | 424/190.1 |
| 2005/0287149 | A1 * | 12/2005 | Keler et al. | 424/164.1 |
| 2006/0019323 | A1 * | 1/2006 | Leclerc et al. | 435/7.32 |
| 2006/0035909 | A1 * | 2/2006 | Fuksova et al. | 514/261.1 |
| 2006/0099169 | A1 * | 5/2006 | Charmot et al. | 424/78.27 |
| 2006/0159697 | A1 * | 7/2006 | Leclerc et al. | 424/190.1 |
| 2006/0258842 | A1 * | 11/2006 | Groen et al. | 530/350 |
| 2006/0292161 | A1 * | 12/2006 | Betsou et al. | 424/164.1 |
| 2007/0059272 | A1 * | 3/2007 | Alverdy | 424/78.3 |
| 2008/0063647 | A1 * | 3/2008 | Morrow et al. | 424/164.1 |
| 2008/0124746 | A1 * | 5/2008 | Tang et al. | 435/7.32 |
| 2009/0093519 | A1 * | 4/2009 | Schein et al. | 514/311 |
| 2009/0234011 | A1 * | 9/2009 | Goldstein | 514/563 |
| 2010/0035867 | A1 * | 2/2010 | Guerrant et al. | 514/225.8 |
| 2010/0075350 | A1 * | 3/2010 | Zegzouti et al. | 435/8 |
| 2010/0119520 | A1 * | 5/2010 | Chen et al. | 424/142.1 |
| 2011/0065782 | A1 * | 3/2011 | Malliavin et al. | 514/447 |
| 2011/0110954 | A1 * | 5/2011 | James et al. | 424/150.1 |
| 2012/0010233 | A1 * | 1/2012 | Schein et al. | 514/290 |

FOREIGN PATENT DOCUMENTS

| | | | |
|---|---|---|---|
| WO | 2005/070419 | * | 8/2005 |
| WO | 2005070419 | A1 | 8/2005 |

OTHER PUBLICATIONS

Peterkofsky, Alan et al, PNAS USA, vol. 71(6), pp. 2324-2328, Jun. 1974, Glucose inhibition of Adenylate Cyclase in Intact Cells of *Escherichia coli* B.*

Desi, K. G. et al, Bioorganic and Medicinal Chemistry, vol. 14, pp. 8271-8279, 2006, Green route for the heterocyclization of 2-mercaptobenzimidazole into B-lactum segment derivative containing CONH-bridge with benzimidazole: Screening in vitro antimicrobial activity with various microorganisms.*

Jones, AM et al, Thorax, 2003, vol. 58, pp. 525-527, Identification of airborne disseminatin of epidemic multiresistant strains of *Pseudomonas aeruginosa* at a CF centre during a cross infection outbreak.*

Steegborn, Clemens et al, A Novel Mechanism for Adenylyl Cyclase Inhibition from the crystal structure of its complex with Catechol Estrogen, The Journal of Biological Chemistry, vol. 280(36), Sep. 9, 2005, pp. 31754-31759.*

Mouallem, M et al, Infection and Immunity, Nov. 1990, vol. 58(11), pp. 3759-3764, *Bordetella pertussis* Adenylate Cyclase toxin: Intoxication of Host cells by Bacterial Invasion.*

Stipa, G et al, Medical Hypotheses, 2006, vol. 67, pp. 1363-1371, Sporadic amyotrophic laterial sclerosis as an infectious disease: A possible role of cyanobacteria?*

Saini, Shamsher S. et al, Inflammation, vol. 27(2), Apr. 2003, pp. 79-88, The Cox-2 Specific Inhibitor Celcoxib Inhibits Adenylyl Cyclase.*

Editorial, Journal of Medical Microbiology, Cyanobacteria and human health, vol. 36, 1992, pp. 301-302.*

Gregg, John P. et al, Valley News Staff Writer, ALS Formums, Disese Cluster Found at Lake, Researchers Seek Link Between Mascoma ALS, Algae, Jun. 10, 2009, pp. 1-15.*

Shoshani, Illana et al, The Journal of Biological Chemistry, vol. 274(49), Dec. 3, 1999, pp. 34742-34744, Inhibition of adenylyl cyclase by acyclic nucleoside phosphonate antiviral agents.*

Shen, Y et al, PNAS, Mar. 2, 2004, vol. 101(9), pp. 3242-3247, Selective inhibition of anthrax edema factor by adefovir, a drug for chronic hepatitis B virus infection.*

Tillman, Hans L. et al, Successful treatment of fibrosing Cholestatic hepatitis using adefovir dipivoxil in a patient with cirrhosis and renal insufficiency, Liver Transplantation, vol. 9(2), pp. 191-196, Feb. 2003.*

Paccani, Silvia R. et al, Anthrax toxins suppress T-lymphocyte activation by disrupting antigen receptor signaling, JEM, vol. 201(3), pp. 325-321, Feb. 7, 2005.*

Guo, Q et al, Structural basis for the interaction of *Bordetella pertussis* adenylyl cyclase toxin with calmodulin, The EMBO Journal 2005, vol. 24, pp. 3190-3201.*

Cereto, F et al, Aliment. Pharmacol. Ther. 2003, vol. 17, pp. 695-701, *E. coli* spontaneous bacterial peritonitis.*

Smith et al, Mar. 2004, Infection and Immunity, vol. 72(3), pp. 1677-1684.*

Gentile, F., et al., "*Bordetella pertussis* adenylate cyclase: preparation into host cells", European Journal of Biochemistry, (1988), vol. 175, pp. 447-453.

Lee, Y., et al. "Discovery of a small molecule that inhibits the interaction of anthrax edema factor with its cellular activator, calmodulin", Chemistry & Biology (2004), vol. 11, pp. 1139-1146.

Little, S. F., et al., "Structure-function analysis of *Bacillus anthracis* edema factor by using monoclonal antibodies", Biochemical and Biophysical Research Communication (1994), vol. 199:2, pp. 676-682.

Soelaiman, S., et al., "Structure-based inhibitor discovery against adenylyl cyclase toxins from pathogenic bacteria that cause anthrax and whooping cough", J. Biological Chemistry (2003) vol. 278:28, pp. 2599-25997.

Ausubel, F. M et al Eds., Current Protocols in Molecular Biology (1987), John Wiley & Sons, Inc., Publishers, USA (Table of Contents).

Cann, M.J. et al., "A Defined Subset of Adenylyl Cyclases Is Regulated by Bicarbonate Ion", J. Biological Chemistry (2003), vol. 278:37, pp. 35033-35038.

Carter, R. et al., "Plasmodia of Rodents", ch. 8, pp. 359-465 in Parasitic Protozoa (1977), Academic Press, Publishers, USA.

Chien, M. et al., "The Genomic Sequence of the Accidental Pathogen *Legionella pneumophila*", Science (2004), vol. 305, pp. 1966-1968.

Church, D.C., Livestock Feeds and Feeding (1977), D.C. Church, Publisher, USA (Table of Contents).

Cornelis, G. R. et al., "Assembly and Function of Type III Secretory Systems" Annu. Rev. Microbiol (2000), vol. 54, pp. 735-774.

Cramton, E.W. et al., Applied Animal Nutrition: The use of Feedstuffs in the Formulation of Livestock Rations, (2nd ed. 1961), W.H. Freeman and Company, Publishers, USA (Table of Contents).

Dolin, P.J. et al., "Global Tuberculosis Incidence and Mortality During 1990-2000", Bul. of the WHO (1994), vol. 72:2, pp. 213-220.

Galán, J.E. et al., "Type III Secretion Machines: Bacterial Devices for Protein Delivery into Host Cells", Science (1999), vol. 284, pp. 1322-1328.

Gennaro, A. R ed., Remington's Pharmaceuticals Sciences, Practice of the Science and Pharmacy (1995), Mack Publishing Company, Publishers, USA (Table of Contents).

(56) References Cited

OTHER PUBLICATIONS

Harper, J.F. et al., "Femtomole Sensitive Radioimmunoassay for Cyclic AMP and Cyclic GMP After 2'0 Acetylation by Acetic Anhydride in Aqueous Solution", J. Cyclic Nuc. Res. (1975), vol. 1:1, pp. 207-218.

Kamenetsky, M. et al., "Molecular Details of cAMP Generation in Mammalian Cells: A Tale of Two Systems", J. Mol. Biol. (2006), vol. 362, pp. 623-639.

Kozliak, E.I. et al., "Role of Bicarbonate/CO2 in the Inhibition of *Escherichia coli* Growth by Cyanate", J. Bacteriology (1995), vol. 177:11, pp. 3213-3129.

Lathem, W.W. et al., "Progression of Primary Pneumonic Plague: A Mouse Model of Infection, Pathology, and Bacterial Transcriptional Activity", PNAS (2005), vol. 102:49, pp. 17786-17791.

Litvin, T.N. et al., "Kinetic Properties of "Soluble" Adenylyl Cyclase", J. Biological Chemistry (2003), vol. 278:18, pp. 15922-15926.

Nordstedt, C. et al., "A Modification of a Protein-Binding Method for Rapid Quantification of cAMP in Cell-Culture Supernatants and Body Fluid", Anal. BioChem (1990), vol. 186, pp. 231-234.

Salomon, Y. et al., "A Highly Sensitive Adenylate Cyclase Assay", Anal. BioChem. (1974), vol. 58, pp. 541-548.

Sambrook, J. et al., eds. Molecular Cloning: A Laboratory Manua, (2nd ed. 1989), Cold Spring Harbor Laboratory Press, Publishers, USA (Table of Contents).

Savkovic, S.D. et al., "Mouse Model of Enteropathogenic *Escherichia coli* Infection", Infection and Immunity (2005), vol. 73:2, pp. 1161-1170.

Savkovic, S.D. et al., "Attachment of a Noninvasive Enteric Pathogen, Enteropathogenic *Escherichia coli*, to Cultured Human Intestinal Epithelial Monolayers Induces Transmigration of Neutrophils", Infection and Immunity (1996), vol. 64:11, pp. 4480-4487.

Siles-Lucs, M. et al., "Cestode Parasites: Application of In Vivo and In Vitro Models for Studies on the Host-Parasite Relationship" Advances in Parasitology (2002), vol. 51, pp. 133-230.

Steiner, A. et al., "Radioimmunoassay for the Measurement of Adenosine 3',5'-Cylic Phosphate", PNAS (1969), vol. 64, pp. 367-373.

Vassella, E. et al., "Differentiation of African Trypanosomes is Controlled by a Density Sensing Mechanism Which Signals Cell Cycle Arrest via the cAMP Pathway", J. Cell Science (1997), vol. 110, pp. 2661-2671.

Wolfgang, M.C. et al., "Coordinate Regulation of Bacterial Virulence Genes by a Novel Adenylate Cyclase-Dependent Signaling Pathway", Dev. Cell (2003), vol. 4, pp. 253-263.

Cann, M.J., Signalling Through Cyclic Nucleotide Monophosphates in Cyanobacteria, New Phytologist (2003), vol. 161, pp. 23-34.

Jonas D. et al., "Development and Mechanism of Fluoroquinolone Resistance in *Legionella pneumophila*" JAC (2003), vol. 51, pp. 275-280.

Lowrie, D.B. et al., "*Mycobacterium microti* May Protect Itself From Intracellular Destruction by Releasing Cyclic AMP into Phagosomes", Nature (1975), vol. 254, pp. 600-602.

Lowrie, D.B. et al., "Phagosome-Lysosome Fusion and Cyclic Adenosine 3':5'-Monophosphate in Macrophages Infected with *Mycobacterium microti, Mycobacterium bovis* BCG or *Mycobacterium lepraemrium*" JGM (1979), vol. 110, pp. 431-441.

Nguyen, H.D. et al., "Synthesis and Structure of Some Derivatives of (Benzothiazol-2-Ylthio)Acetylhydrazine", JC (2006), vol. 44:4, pp. 524-259.

Nicoloff, H. et al., "Repression of the pyr Operon in *Lactobacillus plantarum* Prevents Its Ability to Grow at Low Carbon Dioxide Levels" JB (2005), vol. 187:6, pp. 2093-2104.

Patani, G.A. et al., "Bioisosterism: A Rational Approach in Drug Design", Chem. Rev. (1996), vol. 96, pp. 3147-3176.

Rajagopal, M. et al., "Low Pressure Co2 Storage of Raw Milk: Microbiological Effects", J. Dairy Sci. (2005), vol. 88, pp. 3130-3138.

\* cited by examiner

ADENYLYL CYCLASES AS NOVEL TARGETS FOR ANTIBACTRIAL INTERVENTIONS

CROSS REFERENCE TO RELATED APPLICATIONS

The present application claims the benefit of the following U.S. Provisional Patent Application No. 60/880,277, filed Jan. 12, 2007. The contents of this applications is incorporated herein by reference.

FEDERAL FUNDING

This invention was made with government support under contract numbers AI64842, GM62328 and HD42060 awarded by NIH. The government has certain rights in the invention.

FIELD OF THE INVENTION

The present invention relates to a method of preventing or treating a disease caused by bacterial infection by administering an effective amount of a modulator of bacterial adenylyl cyclase. The invention also provides pharmaceutical compositions useful for preventing or treating a disease, with the compositions containing a therapeutically effective amount of a modulator of bacterial adenylyl cyclase. The invention also provides screening methods for identifying selective modulators of bacterial adenylyl cyclase that do not substantially modulate adenylyl cyclase of the subject. The invention also provides methods for culturing bacterial pathogens and methods for inducing the pathogenic state in vitro.

BACKGROUND OF THE INVENTION

Cyclic-3',5'-adenosine monophosphate (cAMP) mediates cellular responses to nutritional conditions and extracellular conditions in organisms from bacteria to humans. Cyclic AMP is synthesized from adenosine triphosphate (ATP) by adenylyl cyclase, and it is rapidly destroyed by cyclic AMP phosphodiesterases that hydrolyze cAMP to form adenosine 5'-monophosphate (5'-AMP). In a non-responding cell, a basal level of cAMP synthesis is balanced by the rate of its breakdown. The concentration of cyclic AMP inside a cell can change by more than twenty fold in seconds in response to extracellular signals. These rapid responses arise because the activity of the adenylyl cyclase is stimulated such that synthesis of the molecule overwhelms this normal (usually static) rate of breakdown.

Adenylyl cyclase is a group of enzymes that catalyze the conversion of ATP to cAMP and pyrophosphate. Six classes of adenylyl cyclase enzymes have been identified based upon protein sequence and properties. Class I adenylyl cyclases are found primarily in enteric bacteria. Class II adenylyl cyclases include the toxins secreted by pathogens such as edema factor (EF) from *Bacillus anthracis* (which causes anthrax), CyaA from *Bordetella pertussis* (the cause of whooping cough), and ExoY from *Pseudomonas aeruginosa* (the cause of various nosocomial infections). Class III is the largest known group and consists of cyclases found in bacteria, archaea and eukaryotes. The class IV enzymes are found in archaeal organisms, and also in some bacteria including the plague-causing *Yersinia pestis*. Class V is comprised of adenylyl cyclase from the strict anaerobic bacterium *Prevotella ruminicola*. Class VI is found in the nitrogen fixing bacteria *Rhizobium etli*. All six classes of enzymes are present in bacteria, while only enzymes belonging to class III have been described in eukaryotes.

In mammalian cells, cAMP is produced by two related families of class III adenylyl cyclase, transmembrane adenylyl cyclases (tmAC) and soluble adenylyl cyclases (sAC). These two families differ in sub-cellular localization, and respond to different regulators (for a review see Kamenetsky et al., *J. Mol. Biol.* Vol. 362, pp. 623-39, 2006). The primary regulators for tmACs are hetrotrimeric G proteins, which transmit extracellular signals via G protein-coupled receptors in response to hormonal stimuli. In contrast, sACs are regulated by intracellular bicarbonate and calcium.

In bacteria, adenylyl cyclase generates cAMP in response to characteristics of the local environment. For example, in the bacteria, *Escherichia coli*, cAMP levels are associated with the nutritional environment surrounding the bacteria. In an environment with plentiful glucose, cAMP levels are at their lower, non-stimulated level. When energy sources are limiting, there is a significant increase in intracellular cAMP levels.

During pathogenesis in a host, an infecting bacteria is challenged to respond to a diverse and dynamic set of environmental conditions. A variety of pathogens exploit this dramatic environmental shift as a signal to alter their growth and virulence. For example, there is a 150-fold difference in $CO_2$ concentration inside the human (or animal) body (5% $CO_2$) compared to the atmosphere (0.03% $CO_2$). When infectious micro-organisms sense this difference, they tailor their genetic program to one most suitable for being inside an infectible host.

Bacteria that are resistant to one or more antibiotics, which make some diseases particularly hard to control, have become increasingly widespread. In fact, virtually all significant bacterial infections in the world are becoming resistant to the current antibiotic treatment of choice. Diseases such as tuberculosis, gonorrhea, malaria, and childhood ear infections are now more difficult to treat than they were just a few decades ago. Drug resistance is an especially difficult problem in clinical settings, such as hospitals. Thus, in the ongoing endeavor to prevent and treat infection by bacteria, there is a great need for novel methods for treating and preventing infection by bacteria.

SUMMARY OF THE INVENTION

In one aspect, the present invention features a method for the treatment of a subject with a disease caused by infection by bacteria by administering to the subject a therapeutic amount of a modulator of a bacterial adenylyl cyclase.

The invention also provides a method for the treatment of a subject with a disease caused by infection by bacteria by administering to the subject a therapeutic amount of a modulator of a bacterial adenylyl cyclase, wherein the amount of the modulator administered is effective at substantially preventing the bacteria from changing to a pathogenic state from a non-pathogenic state, or wherein the amount of the modulator administered causes the bacteria to substantially revert to a non-pathogenic state from a pathogenic state. Preventing bacteria from entering a pathogenic state involves preventing the expression of genes and/or the production of proteins that are associated with pathogenesis, and preventing changes associated with the pathogenic state such as morphological changes, changes in shape, toxin production, germination, changes in growth rate, and formation of biofilms.

The invention also provides a method for the treatment of a subject with a disease caused by infection by bacteria, by administering to the subject a therapeutic amount of a modulator of a bacterial adenylyl cyclase, wherein the modulator of the bacterial adenylyl cyclase inhibits the bacterial adenylyl cyclase. In other embodiments, the modulator activates the bacterial adenylyl cyclase.

The invention also provides a method for the treatment of a subject with a disease caused by infection by bacteria, by administering to the subject a therapeutic amount of a modulator of a bacterial adenylyl cyclase, wherein the modulator of the bacterial adenylyl cyclase has a substantially bactericidal effect upon the infecting bacteria. In other embodiments the modulator of the bacterial adenylyl cyclase has a substantially bacteriostatic effect upon the infecting bacteria. In certain embodiments, the amount of modulator of the bacterial adenylyl cyclase does not kill the infecting bacteria. In other embodiments, the amount of modulator of the bacterial adenylyl cyclase does not inhibit or prevent the growth of the bacteria.

The invention also provides a method for the treatment of a subject with a disease caused by infection by bacteria, by administering to the subject a therapeutic amount of a modulator of a bacterial adenylyl cyclase, wherein the modulator of the bacterial adenylyl cyclase affects more than one bacterial adenylyl cyclase of an infecting bacteria. The invention also provides that the modulator of the bacterial adenylyl cyclase affects more than one bacterial adenylyl cyclase of more than one infecting bacteria. In one embodiment, the invention also provides that the modulator of the bacterial adenylyl cyclase does not affect whether the bacteria enters the pathogenic state.

The invention also provides a method for the treatment of a subject with a disease caused by infection by bacteria, by administering to the subject a therapeutic amount of a modulator of a bacterial adenylyl cyclase, wherein the modulator of bacterial adenylyl cyclase affects the response of the infecting bacterial adenylyl cyclase to $CO_2$. In other embodiments, the modulator affects the response of the infecting bacterial adenylyl cyclase to $HCO_3$. In other embodiments, the modulator affects the response of the infecting bacterial adenylyl cyclase to pH.

The invention also provides a method for the treatment of a subject with a disease caused by infection by bacteria, by administering to the subject a therapeutic amount of a modulator of a bacterial adenylyl cyclase, wherein the modulator of the bacterial adenylyl cyclase affects a Class I, Class III, or Class IV bacterial adenylyl cyclase.

The invention also provides a method for the treatment of a subject with a disease caused by infection by bacteria, by administering to the subject a therapeutic amount of a modulator of a bacterial adenylyl cyclase, wherein the disease is caused by infection by bacteria selected from the group consisting of Gram negative bacteria, Gram negative cocci, Gram negative rods, Gram positive bacteria, Gram positive cocci, and Gram positive rods. In other embodiments, the disease is caused by infection by a spirochete. In other embodiments, the disease is caused by infection by enteric bacteria, for example *Escherichia coli, Salmonella enterica, Shigella, Shigella dysenteriae, Vibrio cholerae, Vibrio vulnificus, Vibrio parahaemolyticus, Virio vulnificus, Campylobacter jejuni, Klebsiella, Enterobacter, Serratia, Proteus, Providencia,* and *Morganella*. In other embodiments, disease is caused by infection by bacteria including, but not limited to, *Bacillus anthracis, Bacillus cereus, Clostridium tetani, Clostrium botulinum, Clostridium perfringens, Clostridium difficile, Mycobacterium tuberculosis Legionella pneumophilla, Vibrio cholera, Staphylococcus aureus, Staphylococcus epidermidis, Staphylococcus saprophyticus, Streptococcus pyogenes, Streptococcus agalactiae, Enterococcus faecalis, Streptococcus bovis, Streptococcus pneumoniae, Streptococcus viridans, Pseudomonas aeruginosa, Corynebacterium diphtheriae, Listeria monocytogenes, Burcella, Francisella tularensis, Yersinia enterocolitica, Yersinia pseudotuberculosis, Yersinia pestis, Pasteurella multocida, Mycobacterium tuberculosis, Mycobacterium bovis, Mycobacterium avium, Mycobacterium leprae, Actinomyces israelii, Nocardia asteroides, Mycoplasma pneumoniae, Treponema pallidum, Borrelia brugdorferi, Leptospira interrogans, Chlamydia psittaci, Chlamydia trachomatis, Chlamydia pneumoniae, R. rickettsii, Coxiella burnetii, R. Prowazekii, Gardnerella vaginalis, Lactobacillus, Peptococcus, Peptostreptococcus, Propionibacterium, Tropheryma, Burkholderia pseudomallei,* and *Burkholderia mallei*. In another embodiment the infecting bacteria is resistant to one or more antibacterial agents.

The invention also provides a method for the treatment of a subject with a disease caused by infection by bacteria, by administering to the subject a therapeutic amount of a modulator of a bacterial adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for the treatment of a subject with a disease caused by infection by bacteria, by administering to the subject a therapeutic amount of a modulator of a bacterial adenylyl cyclase, wherein the subject is at high risk of infection, for example a subject following surgery.

The invention also provides a method for the treatment of a subject with a disease caused by infection by bacteria, by administering to the subject a therapeutic amount of a modulator of a bacterial adenylyl cyclase, wherein the subject is a human. In another embodiment, the human is immune-compromised. The immune compromised human may be infected with HIV, undergoing chemotherapy, affected by a blood cancer, a transplant recipient, receiving immunosuppressant medication, receiving opioid medication, or a burn victim.

The invention also provides a method for the treatment of a subject with a disease caused by infection by bacteria, by administering to the subject a therapeutic amount of a modulator of a bacterial adenylyl cyclase, wherein the subject is a human who has an opportunistic lung infection. In a further embodiment the human who has an opportunistic lung infection has cystic fibrosis, asthma, or sarcoidosis. In another embodiment, the human has been exposed to airborne infectious agents such as *B. anthracis* or *M. tuberculosis.*

The invention also provides a method for the treatment of a subject with a disease caused by infection by bacteria, by administering to the subject a therapeutic amount of a modulator of a bacterial adenylyl cyclase, wherein the modulator of bacterial adenylyl cyclase does not substantially inhibit the adenylyl cyclases of the subject. In this embodiment, the modulator of bacterial adenylyl cyclase is selective relative to subject's adenylyl cyclase(s). Preferably, the modulator of bacterial adenylyl cyclase is sufficiently selective against the subject's adenylyl cyclase that a therapeutic effect upon the infecting bacteria can be achieved without toxic regulation of the subject's adenylyl cyclase occurring.

The invention also provides a method of treating a bacterial infection in a subject, mediated by adenylyl cyclase of a bacteria in a subject, comprising, modulating the adenylyl cyclase of the bacteria.

The invention also provides a method of inhibiting the adenylyl cyclase of a bacteria, the method comprising: contacting eukaryotic cells with a compound that inhibits adenylyl cyclase of the bacteria.

The invention also provides a method for the treatment of a subject with a disease caused by infection by bacteria, by administering to the subject a therapeutic amount of a modulator of a bacterial adenylyl cyclase, wherein the modulator of bacterial adenylyl cyclase is selected from the group consisting of small molecules, aptamers, and interfering RNA.

The invention also provides a method for the treatment of a subject with a disease caused by infection by bacteria, by administering to the subject a therapeutic amount of a modulator of a bacterial adenylyl cyclase, wherein the modulator of bacterial adenylyl cyclase is selected from the compounds listed in Table 1, or a combination thereof.

The invention also provides a method for the treatment of a subject with a disease caused by infection by bacteria, by administering to the subject a therapeutic amount of a modulator of a bacterial adenylyl cyclase, wherein the modulator of bacterial adenylyl cyclase is selected from catechol estrogens and derivatives thereof.

The invention also provides a method for the treatment of a subject with a disease caused by infection by bacteria, by administering to the subject a therapeutic amount of a modulator of a bacterial adenylyl cyclase in combination with one or more additional therapeutic agents. In a further embodiment, the additional therapeutic agent is an antibacterial agent.

The invention provides a method for preventing disease in a subject caused by bacterial infection by administering to the subject a therapeutic amount of a modulator of a bacterial adenylyl cyclase.

The invention also provides a method for preventing disease in a subject caused by bacterial infection by administering to the subject a therapeutic amount of a modulator of a bacterial adenylyl cyclase wherein, the amount of modulator of bacterial adenylyl cyclase administered is effective at substantially preventing the bacteria from changing to a pathogenic state from a non-pathogenic state, or wherein the amount of the inhibitor of bacterial adenylyl cyclase administered causes the bacteria to substantially revert to a non-pathogenic state from a pathogenic state. Preventing the bacteria from entering a pathogenic state includes preventing changes associated with the pathogenic state such as morphological changes, changes in shape, toxin production, germination, changes in growth rate, and formation of biofilms. Further, the pathogenic state involves expression of genes and the production of proteins that are associated with pathogenesis (for example but not limited to production of toxins and secretion systems).

The invention also provides a method for preventing disease in a subject caused by bacterial infection by administering to the subject a therapeutic amount of a modulator of a bacterial adenylyl cyclase, wherein the modulator of the bacterial adenylyl cyclase inhibits the bacterial adenylyl cyclase. In other embodiments, the modulator activates the bacterial adenylyl cyclase.

The invention also provides a method for preventing disease in a subject caused by bacterial infection by administering to the subject a therapeutic amount of a modulator of a bacterial adenylyl cyclase, wherein the modulator of the bacterial adenylyl cyclase has a substantially bactericidal effect upon the infecting bacteria. In other embodiments the modulator of the bacterial adenylyl cyclase has a substantially bacteriostatic effect upon the infecting bacteria. In certain embodiments, the amount of modulator of the bacterial adenylyl cyclase does not kill the infecting bacteria. In other embodiments, the amount of modulator of the bacterial adenylyl cyclase does not inhibit or prevent the growth of the bacteria.

The invention also provides a method for preventing disease in a subject caused by bacterial infection by administering to the subject a therapeutic amount of a modulator of a bacterial adenylyl cyclase, wherein the modulator of the bacterial adenylyl cyclase affects more than one bacterial adenylyl cyclase of an infecting bacteria. The invention also provides that the modulator of the bacterial adenylyl cyclase affects more than one bacterial adenylyl cyclase of more than one infecting bacteria. In one embodiment, the invention also provides that the modulator of the bacterial adenylyl cyclase does not affect whether the bacteria enters the pathogenic state.

The invention also provides a method for preventing disease in a subject caused by bacterial infection by administering to the subject a therapeutic amount of a modulator of a bacterial adenylyl cyclase, wherein the modulator of bacterial adenylyl cyclase affects the response of the infecting bacterial adenylyl cyclase to $CO_2$. In other embodiments, the modulator affects the response of the infecting bacterial adenylyl cyclase to $HCO_3$. In other embodiments, the modulator affects the response of the infecting bacterial adenylyl cyclase to pH.

The invention also provides a method for preventing disease in a subject caused by bacterial infection by administering to the subject a therapeutic amount of a modulator of a bacterial adenylyl cyclase, wherein the modulator of the bacterial adenylyl cyclase affects a Class I, Class III, or Class IV bacterial adenylyl cyclase.

The invention also provides a method for preventing disease in a subject caused by bacterial infection by administering to the subject a therapeutic amount of a modulator of a bacterial adenylyl cyclase, wherein the disease is caused by infection by bacteria selected from the group consisting of Gram negative bacteria, Gram negative cocci, Gram negative rods, Gram positive bacteria, Gram positive cocci, and Gram positive rods. In other embodiments, the disease is caused by infection by a spirochete. In other embodiments, the disease is caused by infection by enteric bacteria, for example *Escherichia coli, Salmonella enterica, Shigella, Shigella dysenteriae, Vibrio cholerae, Vibrio vulnificus, Vibrio parahaemolyticus, Virio vulnificus, Campylobacter jejuni, Klebsiella, Enterobacter, Serratia, Proteus, Providencia,* and *Morganella*. In other embodiments, disease is caused by infection by bacteria including, but not limited to, *Bacillus anthracis, Bacillus cereus, Clostridium tetani, Clostrium botulinum, Clostridium perfringens, Clostridium difficile, Mycobacterium tuberculosis Legionella pneumophilla, Vibrio cholera, Staphylococcus aureus, Staphylococcus epidermidis, Staphylococcus saprophyticus, Streptococcus pyogenes, Streptococcus agalactiae, Enterococcus faecalis, Streptococcus bovis, Streptococcus pneumoniae, Streptococcus viridans, Pseudomonas aeruginosa, Corynebacterium diphtheriae, Listeria monocytogenes, Burcella, Francisella tularensis, Yersinia enterocolitica, Yersinia pseudotuberculosis, Yersinia pestis, Pasteurella multocida, Mycobacterium tuberculosis, Mycobacterium bovis, Mycobacterium avium, Mycobacterium leprae, Actinomyces israelii, Nocardia asteroides, Mycoplasma pneumoniae, Treponema pallidum, Borrelia brugdorferi, Leptospira interrogans, Chlamydia psittaci, Chlamydia trachomatis, Chlamydia pneumoniae, R. rickettsii, Coxiella burnetii, R. Prowazekii, Gardnerella vaginalis, Lactobacillus, Peptococcus, Peptostreptococcus, Propionibacterium, Tropheryma, Burkholderia pseudomallei,* and *Burkholderia mallei*. In another embodiment the infecting bacteria is resistant to one or more antibacterial agents.

The invention also provides a method for preventing disease in a subject caused by bacterial infection by administering to the subject a therapeutic amount of a modulator of a bacterial adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for preventing disease in a subject caused by bacterial infection by administering to the subject a therapeutic amount of a modulator of a bacterial adenylyl cyclase, wherein the subject is at high risk of infection, for example a subject following surgery.

The invention also provides a method for preventing disease in a subject caused by bacterial infection by administering to the subject a therapeutic amount of a modulator of a bacterial adenylyl cyclase, wherein the subject is a human. In another embodiment, the human is immune-compromised. The immune compromised human may be infected with HIV, undergoing chemotherapy, affected by a blood cancer, a transplant recipient, receiving immunosuppressant medication, receiving opioid medication, or a burn victim.

The invention also provides a method for preventing disease in a subject caused by bacterial infection by administering to the subject a therapeutic amount of a modulator of a bacterial adenylyl cyclase, wherein the subject is a human who has an opportunistic lung infection. In a further embodiment the human who has an opportunistic lung infection has cystic fibrosis, asthma, and sarcoidosis. In another embodiment the human has been exposed to airborne infectious agents such as anthracis or tuberculosis.

The invention also provides a method for preventing disease in a subject caused by bacterial infection by administering to the subject a therapeutic amount of a modulator of a bacterial adenylyl cyclase, wherein the modulator of bacterial adenylyl cyclase does not substantially inhibit the adenylyl cyclases of the subject. In this embodiment, the modulator of bacterial adenylyl cyclase is selective relative to subject's adenylyl cyclase(s). Preferably, the modulator of bacterial adenylyl cyclase is sufficiently selective against the subject's adenylyl cyclase that a therapeutic effect upon the infecting bacteria can be achieved without toxic regulation of the subject's adenylyl cyclase occurring.

The invention also provides a method of preventing a bacterial infection in a subject, mediated by adenylyl cyclase of a bacteria in a subject, comprising, modulating the adenylyl cyclase of the bacteria.

The invention also provides a method for preventing disease in a subject caused by bacterial infection by administering to the subject a therapeutic amount of a modulator of a bacterial adenylyl cyclase, wherein the modulator of bacterial adenylyl cyclase is selected from the group consisting of small molecules, aptamers, and interfering RNA.

The invention also provides a method for preventing disease in a subject caused by bacterial infection by administering to the subject a therapeutic amount of a modulator of a bacterial adenylyl cyclase, wherein the modulator of bacterial adenylyl cyclase is selected from the compounds listed in Table 1 or a combination thereof.

The invention also provides a method for preventing disease in a subject caused by bacterial infection by administering to the subject a therapeutic amount of a modulator of a bacterial adenylyl cyclase, wherein the modulator of bacterial adenylyl cyclase is selected from catechol estrogens and derivatives thereof.

The invention also provides a method for preventing disease in a subject caused by bacterial infection by administering to the subject a therapeutic amount of a modulator of a bacterial adenylyl cyclase in combination with one or more additional therapeutic agents. In a further embodiment, the additional therapeutic agent is an antibacterial agent.

In one aspect, the present invention features a pharmaceutical composition comprising a therapeutically effective amount of a modulator of a bacterial adenylyl cyclase.

The invention also provides a pharmaceutical composition comprising a therapeutically effective amount of a modulator of a bacterial adenylyl cyclase, wherein the amount of the modulator administered is effective at substantially preventing the bacteria from changing to a pathogenic state from a non-pathogenic state, or wherein the amount of the modulator administered causes the bacteria to substantially revert to a non-pathogenic state from a pathogenic state. Preventing the bacteria from entering a pathogenic state includes preventing changes associated with the pathogenic state such as morphological changes, changes in shape, toxin production, germination, changes in growth rate, and formation of biofilms. Further, the pathogenic state involves expression of genes and the production of proteins that are associated with pathogenesis.

In one embodiment, the pharmaceutical composition is delivered in a pharmaceutically acceptable excipient and may be in any pharmaceutically acceptable dosage form, such as oral or parenteral dosage forms. Further, the oral dosage forms may be in the form of tablets, capsules, or liquids.

The invention also provides a pharmaceutical composition comprising a therapeutically effective amount of a modulator of a bacterial adenylyl cyclase, wherein the modulator inhibits the bacterial adenylyl cyclase. In other embodiments, the modulator activates the bacterial adenylyl cyclase.

The invention also provides a pharmaceutical composition comprising a therapeutically effective amount of a modulator of a bacterial adenylyl cyclase, wherein the modulator of the bacterial adenylyl cyclase has a substantially bactericidal effect upon the infecting bacteria. In other embodiments, the modulator of the bacterial adenylyl cyclase has a substantially bacteriostatic effect upon the infecting bacteria. In certain embodiments, the amount of modulator of the bacterial adenylyl cyclase does not kill the infecting bacteria. In other embodiments, the amount of modulator of the bacterial adenylyl cyclase does not inhibit or prevent the growth of the bacteria.

The invention also provides a pharmaceutical composition comprising a therapeutically effective amount of a modulator of a bacterial adenylyl cyclase, wherein the modulator of the bacterial adenylyl cyclase affects more than one bacterial adenylyl cyclase of an infecting bacteria. The invention also provides that the modulator of the bacterial adenylyl cyclase affects more than one bacterial adenylyl cyclase of more than one infecting bacteria. The invention also provides that the modulator of the bacterial adenylyl cyclase does not affect whether the bacteria enters the pathogenic state.

The invention also provides a pharmaceutical composition comprising a therapeutically effective amount of a modulator of a bacterial adenylyl cyclase, wherein the modulator of bacterial adenylyl cyclase affects the response of the infecting bacterial adenylyl cyclase to $CO_2$. In other embodiments, the modulator affects the response of the infecting bacterial adenylyl cyclase to $HCO_3$. In other embodiments, the modulator affects the response of the infecting bacterial adenylyl cyclase to pH.

The invention also provides a pharmaceutical composition comprising a therapeutically effective amount of a modulator of a bacterial adenylyl cyclase, wherein the modulator of the bacterial adenylyl cyclase affects a Class I, Class III, or Class IV bacterial adenylyl cyclase.

The invention also provides a pharmaceutical composition comprising a therapeutically effective amount of a modulator of a bacterial adenylyl cyclase, wherein the disease is caused by infection by bacteria selected from the group consisting of Gram negative bacteria, Gram negative cocci, Gram negative rods, Gram positive bacteria, Gram positive cocci, and Gram positive rods. In other embodiments, the disease is caused by infection by a spirochete. In other embodiments, the disease is caused by infection by enteric bacteria, for example *Escherichia coli, Salmonella enterica, Shigella, Shigella dysenteriae, Vibrio cholerae, Vibrio vulnificus, Vibrio parahaemolyticus, Virio vulnificus, Campylobacter jejuni, Klebsiella, Enterobacter, Serratia, Proteus, Providencia*, and *Morganella*. In other embodiments, disease is caused by infection by bacteria including, but not limited to, *Bacillus anthracis, Bacillus cereus, Clostridium tetani, Clostrium botulinum, Clostridium perfringens, Clostridium difficile, Mycobacterium tuberculosis Legionella pneumophilla, Vibrio cholera, Staphylococcus aureus, Staphylococcus epidermidis, Staphylococcus saprophyticus, Streptococcus pyogenes, Streptococcus agalactiae, Enterococcus faecalis, Streptococcus bovis, Streptococcus pneumoniae, Streptococcus viridans, Pseudomonas aeruginosa, Corynebacterium diphtheriae, Listeria monocytogenes, Burcella, Francisella tularensis, Yersinia enterocolitica, Yersinia pseudotuberculosis, Yersinia pestis, Pasteurella multocida, Mycobacterium tuberculosis, Mycobacterium bovis, Mycobacterium avium, Mycobacterium leprae, Actinomyces israelii, Nocardia asteroides, Mycoplasma pneumoniae, Treponema pallidum, Borrelia brugdorferi, Leptospira interrogans, Chlamydia psittaci, Chlamydia trachomatis, Chlamydia pneumoniae, R. rickettsii, Coxiella burnetii, R. Prowazekii, Gardnerella vaginalis, Lactobacillus, Peptococcus, Peptostreptococcus, Propionibacterium, Tropheryma, Burkholderia pseudomallei*, and *Burkholderia mallei*. In another embodiment the infecting bacteria is resistant to one or more antibacterial agents.

The invention also provides a pharmaceutical composition comprising a therapeutically effective amount of a modulator of a bacterial adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a pharmaceutical composition comprising a therapeutically effective amount of a modulator of a bacterial adenylyl cyclase, wherein the subject is at high risk of infection, for example a subject following surgery.

The invention also provides a pharmaceutical composition comprising a therapeutically effective amount of a modulator of a bacterial adenylyl cyclase, wherein the subject is a human. In another embodiment, the human is immune-compromised. The immune compromised human may be infected with HIV, undergoing chemotherapy, affected by a blood cancer, a transplant recipient, receiving immunosuppressant medication, receiving opioid medication, or a burn victim.

The invention also provides a pharmaceutical composition comprising a therapeutically effective amount of a modulator of a bacterial adenylyl cyclase, wherein the subject is a human who has an opportunistic lung infection. In a further embodiment the human who has an opportunistic lung infection has cystic fibrosis, asthma, and sarcoidosis. In another embodiment the human has been exposed to airborne infectious agents such as anthracis or tuberculosis.

The invention also provides a pharmaceutical composition comprising a therapeutically effective amount of a modulator of a bacterial adenylyl cyclase, wherein the modulator of bacterial adenylyl cyclase does not substantially inhibit the adenylyl cyclases of the subject. In this embodiment, the modulator of bacterial adenylyl cyclase is selective relative to subject's adenylyl cyclase(s). Preferably, the modulator of bacterial adenylyl cyclase is sufficiently selective against the subject's adenylyl cyclase that a therapeutic effect upon the infecting bacteria can be achieved without toxic regulation of the subject's adenylyl cyclase occurring.

The invention also provides a pharmaceutical composition comprising a therapeutically effective amount of a modulator of a bacterial adenylyl cyclase, directed to treating a bacterial infection in a subject, mediated by adenylyl cyclase of a bacteria in a subject, comprising, modulating the adenylyl cyclase of the bacteria.

The invention also provides a pharmaceutical composition comprising a therapeutically effective amount of a modulator of a bacterial adenylyl cyclase, wherein the modulator of bacterial adenylyl cyclase is selected from the group consisting of small molecules, aptamers, and interfering RNA.

The invention also provides a pharmaceutical composition comprising a therapeutically effective amount of a modulator of a bacterial adenylyl cyclase, wherein the modulator of bacterial adenylyl cyclase is selected from the compounds listed in Table 1 or a combination thereof.

The invention also provides a pharmaceutical composition comprising a therapeutically effective amount of a modulator of a bacterial adenylyl cyclase, wherein the modulator of bacterial adenylyl cyclase is selected from catechol estrogens and derivatives thereof.

The invention also provides a pharmaceutical composition comprising a therapeutically effective amount of a modulator of a bacterial adenylyl cyclase in combination with one or more additional therapeutic agents. In a further embodiment, the additional therapeutic agent is an antibacterial agent.

In one aspect, the invention provides a method of identifying a selective modulator of a bacterial adenylyl cyclase, the method comprising: testing the modulator against one or more human adenylyl cyclases, testing the modulator against one or more bacterial adenylyl cyclases, and determining the relative selectivity of the modulator for the said adenylyl cyclases.

In one aspect, the invention provides a method for controlling the growth of bacteria in vitro by treating the bacteria with a modulator of bacterial adenylyl cyclase. In one embodiment the modulator of bacterial adenylyl cyclase is an activator that stimulates proliferation of the bacteria in vitro. In a further embodiment, the activator of bacterial adenylyl cyclase is utilized to enhance bacterial growth in fermentation, in bioreactors, and to produce recombinant proteins.

In one embodiment, the bacteria induced by the activator of bacterial adenylyl cyclase to be in the pathogenic state are then used to test inhibitors of bacterial adenylyl cyclase for their inhibitory characteristics.

The invention also provides a method for controlling the growth of bacteria in vitro by treating the bacteria with a modulator of bacterial adenylyl cyclase, wherein the modulator of bacterial adenylyl cyclase induces a pathogenic state in the bacteria in vitro. In a further embodiment, the induced pathogenic state provides a gene expression and protein expression profile associated with pathogenesis of the bacteria in vitro. In another embodiment, the pathogenic form of the bacteria, induced by the modulator of bacterial adenylyl cyclase, is inactivated and used in immunization protocols to induce resistance to infection by the bacteria. In another embodiment, the pathogenic form of the bacteria, induced by the activator, is a source for antigenic proteins associated with the pathogenic state. In these embodiments the bacteria or the antigenic proteins or sugars, as well as subcellular fractions (membrane fractions, etc) are used in immunoprotective preparations for vaccination approaches.

In another embodiment, the invention provides a method of vaccination in which the vaccine comprises an attenuated strain of bacteria. The attenuated strain of bacteria is a deletion mutant (knock-out) of a bacterial adenylyl cyclase wherein the attenuated strain of bacteria is selected from the group consisting of Gram negative bacteria, Gram negative cocci, Gram negative rods, Gram positive bacteria, Gram positive cocci, and Gram positive rods. In other embodiments, the attenuated strain of bacteria is a spirochete. In other embodiments, the attenuated strain of bacteria is an enteric bacteria, for example *Escherichia coli, Salmonella enterica, Shigella, Shigella dysenteriae, Vibrio cholerae, Vibrio vulnificus, Vibrio parahaemolyticus, Virio vulnificus, Campylobacter jejuni, Klebsiella, Enterobacter, Serratia, Proteus, Providencia,* and *Morganella*. In other embodiments, the attenuated strain of bacteria includes, but is not limited to, *Bacillus anthracis, Bacillus cereus, Clostridium tetani, Clostrium botulinum, Clostridium perfringens, Clostridium difficile, Mycobacterium tuberculosis Legionella pneumophilla, Vibrio cholera, Staphylococcus aureus, Staphylococcus epidermidis, Staphylococcus saprophyticus, Streptococcus pyogenes, Streptococcus agalactiae, Enterococcus faecalis, Streptococcus bovis, Streptococcus pneumoniae, Streptococcus viridans, Pseudomonas aeruginosa, Corynebacterium diphtheriae, Listeria monocytogenes, Burcella, Francisella tularensis, Yersinia enterocolitica, Yersinia pseudotuberculosis, Yersinia pestis, Pasteurella multocida, Mycobacterium tuberculosis, Mycobacterium bovis, Mycobacterium avium, Mycobacterium leprae, Actinomyces israelii, Nocardia asteroides, Mycoplasma pneumoniae, Treponema pallidum, Borrelia brugdorferi, Leptospira interrogans, Chlamydia psittaci, Chlamydia trachomatis, Chlamydia pneumoniae, R. rickettsii, Coxiella burnetii, R. Prowazekii, Gardnerella vaginalis, Lactobacillus, Peptococcus, Peptostreptococcus, Propionibacterium, Tropheryma, Burkholderia pseudomallei,* and *Burkholderia mallei*.

The invention also provides a method to substantially disinfect targets by exposing the target to a modulator of bacterial adenylyl cyclase. Targets may be any apparatus or surface on which an individual may desire to reduce or prevent bacterial growth and include, but are not limited to, food processing equipment, and medical devices.

The invention also provides a method of disinfection and/or preserving goods by including an effective amount of a modulator of bacterial adenylyl cyclase. Goods include, but are not limited to, medical devices, foods, beverages, lotions, ointments, eye drops, fabrics, and silk. In a further embodiment, the modulator of bacterial adenylyl cyclase is included as an antibacterial agent in goods including, but not limited to soaps, shampoos, lotions, toothpaste, mouthwash, ointments, hand sanitizers, disinfectants, household cleaners, paints, stains, and metalworking fluids.

DESCRIPTION OF FIGURES

FIG. 1. Increasing concentrations of the KH7.148 compound cause a decrease in the activity of the *Pseudomonas aeruginosa* CyaB adenylyl cyclase. The CyaB was heterologously expressed in *E. coli* as a poly-histidine tagged fusion protein and purified using a nickel column. Adenylyl cyclase activity was determined by measuring cyclic AMP levels using the Correlate-EIA Direct Cyclic AMP assay kit from Assay Designs as per manufacturers instructions.

FIG. 2. Increasing concentrations of the KH7.120 compound cause an increase in the activity of the *Pseudomonas aeruginosa* CyaB adenylyl cyclase. The CyaB was heterologously expressed in *E. coli* as a poly-histidine tagged fusion protein and purified using a nickel column. Adenylyl cyclase activity was determined by measuring cyclic AMP levels using the Correlate-EIA Direct Cyclic AMP assay kit from Assay Designs as per manufacturers instructions.

DETAILED DESCRIPTION OF THE INVENTION

The invention provides a method for preventing or treating a disease by administering an effective amount of a modulator of bacterial adenylyl cyclase.

Adenylyl cyclase is a group of enzymes that catalyze the conversion of ATP to cAMP and pyrophosphate. Six classes of adenylyl cyclase enzymes have been identified based upon protein sequence and properties. Class I adenylyl cyclases are found primarily in enteric bacteria. Class II adenylyl cyclases include the toxins secreted by pathogens such as edema factor (EF) from *Bacillus anthracis* (which causes anthrax), CyaA from *Bordetella pertussis* (the cause of whooping cough), and ExoY from *Pseudomonas aeruginosa* (the cause of various nosocomial infections). Class III is the largest known group and consists of cyclases found in bacteria, archaea and eukaryotes. The class IV enzymes are found in archaeal organisms, and also in some bacteria including the plague-causing *Yersinia pestis*. Class V is comprised of one adenylyl cyclase from the strict anaerobic bacterium *Prevotella ruminicola*. Class VI is found in the nitrogen fixing bacteria *Rhizobium etli*. All six classes of enzymes are present in bacteria, while only enzymes belonging to class III have been described in eukaryotes.

In mammalian cells cAMP is produced by two related families of the class III adenylyl cyclase, transmembrane adenylyl cyclases (tmAC) and soluble adenylyl cyclases (sAC). These two families differ in sub-cellular localization and respond to different regulators. The primary regulators for tmACs are hetrotrimeric G proteins, which transmit extracellular signals via G protein-coupled receptors. In contrast, sACs are regulated by intracellular bicarbonate and calcium.

Carbon dioxide ($CO_2$) is the end product of metabolism in animals. In all physiological systems, $CO_2$ exists in an almost instantaneous equilibrium with bicarbonate and pH ($H^+$ concentration) due to the presence of the enzyme, carbonic anhydrase, which catalyzes the rapid interconversion of carbon dioxide and water into carbonic acid, which dissociates into protons and bicarbonate ions according to the following equation:

$$CO_2 + H_2O \rightleftharpoons H_2CO_3 \rightleftharpoons HCO_3^- + H^+$$

This reaction occurs spontaneously in aqueous solution, but does so slowly. The enzyme carbonic anhydrase greatly increases the rate of the reaction.

During pathogenesis in a host, an infecting microbe is challenged to respond to a diverse and dynamic set of environmental conditions. A variety of pathogenic bacteria have evolved to exploit the dramatic environmental shifts encountered once inside an infectible host as a signal to alter their growth and virulence properties. One such environmental signal that infectious bacteria exploit is the change in concentration of $CO_2$, $HCO_3^-$, and/or pH. There is a 150-fold difference in $CO_2$ concentration inside the human (or animal) body (5% $CO_2$) compared to the atmosphere (0.03% $CO_2$). Because $CO_2$ levels are in equilibrium with the concentration of bicarbonate and pH levels, these infectious bacteria may sense differences in concentrations of $CO_2$, $HCO_3$, or pH levels to detect when they are inside an infectible host.

For example, Group A streptococci activate transcription of the virulence genes emm and scpA in response to higher concentrations of $CO_2$. In the highly pathogenic *Bacillus anthracis*, elevated concentrations of $CO_2$ stimulate germination, capsule biosynthesis, and toxin production. However, little was known about the mechanisms of $CO_2$-sensing in any prokaryotic pathogen. It now appears that the adenylyl cyclases in these organisms responds to changes in $CO_2/HCO_3/pH$. We propose that $CO_2$ sensing via $CO_2/HCO_3/pH$-sensing adenylyl cyclases represents a general paradigm for bacteria to detect when they are in the correct environment (i.e., an infectible host) to elicit the expression of their pathogenic phenotype. Targeting the bacterial adenylyl cyclases, and particularly the $CO_2/HCO_3/pH$-sensing adenylyl cyclases, represents a novel opportunity for the prevention and treatment of bacterial infection.

Bacterial infection may occur due to invasion by pathogenic bacteria or by invasion by bacteria that are opportunistic pathogens. The bacteria may be Gram negative bacteria, such as Gram negative cocci and Gram negative rods, and may be Gram positive bacteria, such as Gram positive cocci, and Gram positive rods. The disease may be caused by infection by a spirochete. Further, the disease may be caused by infection by enteric bacteria, for example *Escherichia coli, Salmonella enterica, Shigella, Shigella dysenteriae, Vibrio cholerae, Vibrio vulnificus, Vibrio parahaemolyticus, Virio vulnificus, Campylobacter jejuni, Klebsiella, Enterobacter, Serratia, Proteus, Providencia*, and *Morganella*. Disease may be caused by infection by other bacteria including *Bacillus anthracis, Bacillus cereus, Clostridium tetani, Clostrium botulinum, Clostridium perfringens, Clostridium difficile, Mycobacterium tuberculosis Legionella pneumophilla, Vibrio cholera, Staphylococcus aureus, Staphylococcus epidermidis, Staphylococcus saprophyticus, Streptococcus pyogenes, Streptococcus agalactiae, Enterococcus faecalis, Streptococcus bovis, Streptococcus pneumoniae, Streptococcus viridans, Pseudomonas aeruginosa, Corynebacterium diphtheriae, Listeria monocytogenes, Burcella, Francisella tularensis, Yersinia enterocolitica, Yersinia pseudotuberculosis, Yersinia pestis, Pasteurella multocida, Mycobacterium tuberculosis, Mycobacterium bovis, Mycobacterium avium, Mycobacterium leprae, Actinomyces israelii, Nocardia asteroides, Mycoplasma pneumoniae, Treponema pallidum, Borrelia brugdorferi, Leptospira interrogans, Chlamydia psittaci, Chlamydia trachomatis, Chlamydia pneumoniae, R. rickettsii, Coxiella burnetii, R. Prowazekii, Gardnerella vaginalis, Lactobacillus, Peptococcus, Peptostreptococcus, Propionibacterium, Tropheryma, Burkholderia pseudomallei*, and *Burkholderia mallei*.

In another embodiment the infecting bacteria is resistant to one or more antibacterial agents such as antibiotics.

*Pseudomonas aeruginosa* is a common cause of respiratory illness and wound infections. It is one of the leading causes of severe nosocomial infections especially in immunocompromised hosts. Current effective treatment for *P. aeruginosa* includes a limited number of antimicrobial agents: antipseudomonal penicillins, some third and fourth generation cephalosporins, a monobactam, some cabapenems, and a fluoroquinolone. Many instances of antibiotic resistance have been described, and multidrug-resistant *Pseudomonas* infections can require treatment with dangerously toxic antimicrobials. Currently, there is a great need for new anti-pseudomonal agents.

*P. aeruginosa* has three adenylyl cyclases: ExoY, a secreted Type II cyclase toxin, CyaA, a class I cyclase, and CyaB, a type III cyclase. Both CyaA and CyaB are thought to serve as a source for cAMP in this pathogen (Wolfgang, 2003). Among the three cyclases in *P. aeruginosa*, however, CyaB has significant homology to sAC, raising the possibility of similar mechanisms of regulation. Interestingly, CyaB was recently identified in a screen designed to determine regulators of type III secretion in *P. aeruginosa* (Wolfgang, 2003). Type III secretion systems (TTSS) are used to inject effector proteins (i.e., toxins) directly into the host cell cytoplasm and are important determinants of virulence in many pathogens. (Cornelis and van Gijsegem 2000 and Galan and Collmer 1999). Mutations in either CyaA or CyaB that disrupt cAMP production led to decreased secretion of the effector protein ExoS and decreased transcription from the ExoS promoter. Additionally, in a cell cytotoxicity assay used to measure TTSS function, a CyaB mutant strain had a more attenuated phenotype than a CyaA mutant strain. Most striking is the finding that CyaA and CyaB mutant strains are less virulent in a mouse model of acute pneumonia (Smith, 2004). In these studies, the CyaB mutant again proved less virulent than the CyaA mutant, suggesting a greater contribution to virulence from CyaB. Sequence comparisons lead us to believe that CyaB is a $CO_2/HCO_3^-$ sensitive cyclase suggesting $CO_2/HCO_3^-$ could be an important regulator of its activity, and CyaA is related to the pH sensitive Class I adenylyl cyclases suggesting it might be sensitive to $CO_2$ induced changes in intracellular pH. Therefore, either or both of the endogenous adenylyl cyclases may represent $CO_2$ sensors in *P. aeruginosa*, which like the other prokaryotic pathogens discussed below, would encounter a dramatic increase in environmental $CO_2$ at its common site of infection, the lung.

*Mycobacterium tuberculosis* is the most common infectious cause of death in adults worldwide (Dolin, 1994). The HIV epidemic has had a drastic impact on its incidence, as *M. tuberculosis* is a particularly common infection in AIDS patients. Treatment for this organism is cumbersome considering the need for combination drug regimens for an extended period of time. Multi-drug resistant strains are becoming increasingly more common and currently, a dire need for new anti-tuberculosis agents exists.

*M. tuberculosis* contains 15 different open reading frames for cyclase enzymes. At least one of these cyclases, Rv1319c, has been shown to respond to changes in bicarbonate concentration (Cann, 2004). Furthermore, evidence suggests an important role for cAMP in tuberculosis pathogenesis. Macrophages allowed to phagocytose *M. tuberculosis* bacilli were reported to have increased levels of cAMP, and impaired phagosome-lysosome fusion (Lowrie, 1975, 1979). In these studies, the authors conclude that the additional cAMP in these cells derives from the ingested bacteria and that this increase underlies the phagosome-lysosome fusion defect.

*Legionella pneumophila* is an aerobic, gram-negative *bacillus* responsible for a potentially fatal atypical pneumonia referred to as Legionnaires' disease. Previously considered a pathogen with rare infections and small, isolated outbreaks, *L. pneumophila* is gaining recognition as a common cause of community-acquired pneumonia and an even more common cause of nosocomial-pneumonia. *L. pneumophila* is usually acquired through an aerosolized contaminated fresh water source such as cooling towers in air-conditioning systems. Current effective treatment of *L. pneumophila* includes a number of available microbial agents such as macrolides, quinolones, and tetracyclines. Despite the effectiveness of the currently available antimicrobial arsenal against this pathogen, the threat of antibiotic resistance still exists (Jonas, 2003).

The recently completed *L. pneumophila* genome revealed five different class III adenylyl cyclases (Chien, 2004). Four of the five cyclases contain lysine and threonine residues predictive for bicarbonate regulation (Cann, 2003). The possibility of cAMP involvement in *legionella* virulence has been postulated (Chien, 2004), but these adenylyl cyclases are largely absent from the *legionella* literature, making them a previously unconsidered target for therapy.

Other prokaryotic pathogens have $CO_2/HCO_3$/pH-sensing adenylyl cyclases. Carbon dioxide is a known signal in bacterial physiology. In certain prokaryotes, it has growth promoting effects (Nikoloff, 2005), where as in others, it inhibits growth (Rajagopal, 2005). For example, in *Escherichia coli*, $CO_2/HCO_3$ has been shown to promote growth through a mechanism independent from carboxylation reactions. (Kozliak, 1995). Many prokaryotic pathogens modify virulence in response to changes in $CO_2/HCO_3$, but to date, little is known about the mechanism of $CO_2$ sensing and the subsequent signal transduction that ultimately leads to an altered phenotype. *E. coli* express a distantly related form of adenylyl cyclase, the so-called Class I adenylyl cyclases. Class I adenylyl cyclases display a pronounced pH sensitivity, and as described above, intracellular pH is another reflection of $CO_2$ changes.

One aspect of the present invention is the prevention or treatment of a bacterial infection by preventing the infecting bacteria from entering the pathogenic state, or by causing the infecting bacteria to revert from a pathogenic state to a non-pathogenic state. A pathogenic state includes any state upon entering the host that confers an advantage to the bacteria or otherwise contributes to the infection, including changing shape or morphology, increase or decrease in growth rate, germination, release of toxins, and formation of biofilm. The pathogenic state also includes expression of genes associated with pathogenesis, such as genes that provide a mechanism to avoid the host immune system, scavenge nutrients, alter motility, damage host tissues, and spread through host cells, tissues, and organs.

Preventing the infecting bacteria from entering a pathogenic state, or causing the bacteria to revert to a non-pathogenic state, can create beneficial effects in preventing and treating bacterial infection including reducing or preventing symptoms of infection, and increasing susceptibility of the invading bacteria to the host's immune system, slowing bacterial growth, preventing the production of endotoxins, preventing the expression of virulence factors, and causing the bacteria to react in manner inconsistent with the host environment and adversely effecting its ability to infect the host.

Modulation of bacterial adenylyl cyclase includes inhibition of the cyclase activity or activation of the cyclase activity. Inhibition of the adenylyl cyclase will reduce cellular levels of cAMP, while activation of the adenylyl cyclase will increase cellular cAMP levels.

The modulator of bacterial adenylyl cyclase may have a bactericidal or bacteriostatic effects. Bacteriostatic refers to an effect that substantially restricts the ability of the bacterium to grow, whereas a bactericidal treatment is substantially lethal to the bacteria. However, it is not necessary for the modulator to kill the bacteria to be effective.

In one embodiment of the invention, the modulator of bacterial adenylyl cyclase may affect one or more adenylyl cyclases of the infecting bacteria. In another embodiment, the modulator affects adenylyl cyclases of multiple infecting bacteria.

In certain embodiments, the modulator of the bacterial adenylyl cyclase affects a Class I, Class III, or Class IV bacterial adenylyl cyclase.

In one embodiment, the invention features a method of inhibiting adenylyl cyclase of a bacteria, the method comprising: contacting eukaryotic cells with a compound that inhibits adenylyl cyclase of the bacteria.

In one embodiment, the invention features a method of treating a bacterial infection in a subject, mediated by adenylyl cyclase of a bacteria in a subject, comprising, modulating the adenylyl cyclase of the bacteria.

For the treatment of a subject, it is preferred that the modulator of bacterial adenylyl cyclase does not substantially inhibit or activate an adenylyl cyclase (or guanylyl cyclase) of the subject. Modulators that are sufficiently selective against the subject's adenylyl cyclase help ensure that a therapeutic effect upon the infecting bacteria can be achieved without adverse regulation of subject's adenylyl cyclase(s).

The term "subject" as used herein refers to any organism in need of treatment, or requiring preventative therapy to prevent infection, with the methods and compositions of the invention. The subject may be a plant or an animal. The subject animal includes fish, birds, or mammals. The subject may be livestock, such as cattle, swine, sheep, poultry, and horses, or pets, such as dogs and cats. The subject may also be a human.

The methods and pharmaceutical compositions of the present invention may also be used to treat or prevent bacterial infection in at-risk subjects, for example preventing or treating infection in a subject following surgery.

A human subject may be otherwise healthy or may have a condition that makes the human particularly susceptible to infection. For example, the human may be immune compromised due to infection with HIV, due to the effects of chemotherapy, due to affliction with a blood cancer, due to immunosuppressant medication, or due to opioid medication. The human may also be a transplant recipient or a burn victim. The human may also be susceptible to infection due to diseases including cystic fibrosis, asthma, and sarcoidosis. The human subject may also be susceptible to an infection due to exposure to airborne infectious agents such as *B. anthracis* or *M. tuberculosis*.

The modulator of bacterial adenylyl cyclase may include, but is not limited to, small molecules, aptamers, small interfering RNA.

In one aspect of the invention, the modulator of bacterial adenylyl cyclase may be an aptamer, which are oligonucleic acid or polypeptide molecules that bind a specific target molecule. They can be synthesized specifically or selected from a pool using various screening methods known in the art for example a yeast two-hybrid system.

In one aspect of the invention, the modulator of bacterial adenylyl cyclase may be a small molecule. In this context, the term small molecule refers to small organic compounds, such as heterocycles, peptides, saccharides, steroids, and the like. The small molecule modulators preferably have a molecular weight of less than about 1500 Daltons, and more preferably less than about 500 Daltons. The compounds may be modified to enhance efficacy, stability, pharmaceutical compatibility, and the like. Candidate modulator compounds from libraries of synthetic or natural compounds can be screened. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). Combinatorial libraries are available or can be prepared according to known synthetic techniques.

Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds may be further modified through conventional chemical and biochemical techniques.

The small molecule modulators of bacterial adenylyl cyclase include but are not limited to small molecules that may interact with the cyclase ATP binding domain, $CO_2/HCO_3^-/pH$ sensing domain, or other regulatory protein binding site. Small molecule libraries can be screened for inhibitory activity using high-throughput biochemical, enzymatic, or cell based assays. The assays can be formulated to detect the ability of a test compound to inhibit or activate the formation of cAMP from ATP.

In certain embodiments the small molecule modulator of bacterial adenylyl cyclase may be selected from catechol estrogens and derivatives thereof. Catechol estrogens are steroid metabolites that elicit physiological responses through binding to a variety of cellular targets. Catechol estrogens may, directly inhibit soluble adenylyl cyclases and transmembrane adenylyl cyclases. Derivatives of catechol estrogens include compounds in which functional groups on the estrogen nucleus have been modified, for example through reduction or oxidation, or a metabolite of catechol estrogens. The catechol estrogens may be further derivatized, for example, as the esters, ethers, oximes, hydrazones, hydroxyamines, carbamate esters, alkoxyesters, carbonate esters, or PEG derivatives.

In other embodiments of the invention, the small, molecule modulator is selected from the compounds disclosed in WO 2005/070419, incorporated herein by reference in its entirety. In other embodiments, the modulator of bacterial adenylyl cyclase is selected the compounds listed in Table 1, or a combination thereof.

The present invention also provides a method for the prevention or treatment of a disease caused by infection by bacteria in a subject, by administering to the subject a composition comprising a therapeutically effective amount of a modulator of the bacterial adenylyl cyclase and a pharmaceutically acceptable excipient.

In another aspect, the present invention provides pharmaceutically acceptable compositions which comprise a therapeutically-effective amount of one or more of the modulators of bacterial adenylyl cyclase, as described above, formulated together with one or more pharmaceutically acceptable excipients. The active ingredient and excipient(s) may be formulated into compositions and dosage forms according to methods known in the art. As described in detail below, the pharmaceutical compositions of the present invention may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

A therapeutically effective amount of the pharmaceutical composition of the present invention is sufficient to treat or prevent disease caused by infection by bacteria. The therapeutically effective amount may prevent the infecting bacteria from changing to a pathogenic state, substantially inhibit disease causing factors associated with the pathogenic state, and/or cause the bacteria to revert from a pathogenic state to a non-pathogenic. The dosage of active ingredient(s) may vary, depending on the reason for use and the individual subject. The dosage may be adjusted based on the subject's weight, the age and health of the subject, and tolerance for the compound or composition.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subjects's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the modulator of bacterial adenylyl cyclase and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste. Flavoring agents and flavor enhancers may make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting, however, they are not subjected to a final tableting step.

The composition of the invention may be administered alone or may be administered in combination with one or more of other therapeutic agents, such as antibiotics. Antibiotics may include, but are not limited to, macrolides (eryrthromycin, azithromaycin, clarithromycin, etc.), β-lactams (penems, cephems, carbapenems and carbacephems, such as penicillin, amoxicillin, ticarcillin, cefazolin, cefaclor, cefepime, ceftriaxone, loracarbef, imipenem, etc.), aminoglycosides (gentamycin, tobramycin, etc.), glycopeptides (vancomycin, etc.), quinolones (ciprofloxacin, levofloxacin, ofloxacin, etc.), tetracyclines (tetracycline, doxycycline, etc.), oxazolidinones (linezolid, etc.), lincosamides (clindamycin, etc.), and chloramphenicol. In a combination therapy, the modulator of bacterial adenylyl cyclase may be administered before, during, or after commencing therapy with another agent (such as an antibiotic agent), as well as any combination thereof, i.e., before and during, before and after, during and after, or before, during and after commencing the additional therapy.

In one embodiment of the invention, the modulator of bacterial adenylyl cyclase may be added to animal feed, for the prevention and/or treatment of bacterial disease in livestock and pets. This may be accomplished by preparing an appropriate feed premix containing the modulator of bacterial adenylyl cyclase in an effective amount and incorporating the premix into the complete ration. Alternatively, an intermediate concentrate or feed supplement containing the active ingredient can be blended into the feed. The way in which such feed premixes and complete rations can be prepared and administered are described in references (such as "Applied Animal Nutrition", W.H. Freedman and CO., San Francisco, U.S.A., 1969 or "Livestock Feeds and Feeding" O and B books, Corvallis, Oreg., U.S.A., 1977).

One aspect of the present invention is a method for controlling bacterial growth in vitro by administering a modulator of bacterial adenylyl cyclase. Increased and decreased growth rate may result from inducing the pathogenic state depending upon the type of bacteria and on the growth conditions. For example, administration of activators of adenylyl cyclase may induce a pathogenic state in bacteria grown in vitro causing the bacteria to grow at an increased rate. Increasing the growth rate of bacteria may be useful in industrial applications for example in fermentation, in bioreactors to generate bacterial products such as biomass and recombinant proteins, and environmental applications for example bioremediation.

Another aspect of the present invention is a method for inducing the pathogenic state in vitro. By exposing bacteria to activators of adenylyl cyclase, changes associated with the pathogenic state can be induced in vitro, including, increased growth rate, growth in various conditions such as increased $CO_2$ levels, and expression of genes and proteins associated with the pathogenic state. In addition, induction of the pathogenic state may then be followed by testing candidate compounds for their ability to inhibit the pathogenic state or aspects of the pathogenic state.

Over-expression of an appropriate adenylyl cyclase gene in the bacteria (e.g. from a cloned plasmid, integrated DNA construct, etc.) can be used to induce the bacteria to enter the pathogenic state. Inducible over-expression can be accomplished by using an inducible promoter. These bacteria can then be used to test inhibitors of adenylyl cyclase.

One aspect of the present invention is a method for inducing a pathogenic state in bacteria in vitro so that the associated pathogenic changes can be exploited to develop vaccines. Modulators of the bacterial adenylyl cyclase that activate the switch to the pathogenic state can be used to achieve the pathogenic form in vitro. The bacteria in the pathogenic state may be expressing antigens unique to the pathogenic state. The pathogenic form of the bacteria can be heat-killed and used in immunization protocols. In addition, the pathogenic form of the bacteria grown in vitro can be a source of antigenic proteins, for example membrane proteins, useful for the development of immunizations against infection by the bacteria.

In another embodiment, the invention provides a method of vaccination in which the vaccine comprises an attenuated strain of bacteria. The attenuated strain of bacteria is a deletion mutant (knock-out) of a bacterial adenylyl cyclase, wherein the attenuated strain of bacteria is selected from the group consisting of Gram negative bacteria, Gram negative cocci, Gram negative rods, Gram positive bacteria, Gram positive cocci, and Gram positive rods. In other embodiments, the attenuated strain of bacteria is a spirochete. In other embodiments, the attenuated strain of bacteria is an enteric bacteria, for example *Escherichia coli, Salmonella enterica, Shigella, Shigella dysenteriae, Vibrio cholerae, Vibrio vulnificus, Vibrio parahaemolyticus, Virio vulnificus, Campylobacter jejuni, Klebsiella, Enterobacter, Serratia, Proteus, Providencia*, and *Morganella*. In other embodiments, the attenuated strain of bacteria includes, but is not limited to, *Bacillus anthracis, Bacillus cereus, Clostridium tetani, Clostrium botulinum, Clostridium perfringens, Clostridium difficile, Mycobacterium tuberculosis Legionella pneumophilla, Vibrio cholera, Staphylococcus aureus, Staphylococcus epidermidis, Staphylococcus saprophyticus, Streptococcus pyogenes, Streptococcus agalactiae, Enterococcus faecalis, Streptococcus bovis, Streptococcus pneumoniae, Streptococcus viridans, Pseudomonas aeruginosa, Corynebacterium diphtheriae, Listeria monocytogenes, Burcella, Francisella tularensis, Yersinia enterocolitica, Yersinia pseudotuberculosis, Yersinia pestis, Pasteurella multocida, Mycobacterium tuberculosis, Mycobacterium bovis, Mycobacterium avium, Mycobacterium leprae, Actinomyces israelii, Nocardia asteroides, Mycoplasma pneumoniae, Treponema pallidum, Borrelia brugdorferi, Leptospira interrogans, Chlamydia psittaci, Chlamydia trachomatis, Chlamydia pneumoniae, R. rickettsii, Coxiella burnetii, R. Prowazekii, Gardnerella vaginalis, Lactobacillus, Peptococcus, Peptostreptococcus, Propionibacterium, Tropheryma, Burkholderia pseudomallei*, and *Burkholderia mallei*.

In another embodiment, the subject is purposely infected with a bacteria, and simultaneously treated with an inhibitor of bacterial adenylyl cyclase so that the bacteria will not become pathogenic, as a means to induce an immune response to said bacteria.

In one embodiment of the invention, the modulator of bacterial adenylyl cyclase is used as a disinfectant and/or preservative in consumer and industrial applications. In one embodiment the modulator of bacterial adenylyl cyclase is used to disinfect targets including any apparatus or surface on which an individual may desire to reduce or prevent bacterial growth such as food processing equipment, and medical devices. In another embodiment, the modulator is added to goods including consumer and industrial goods. Consumer goods include, but are not limited to, foods, beverages, toothpaste, mouthwash, lotions, ointments, fabrics, and silk. In another embodiment, the modulator of bacterial adenylyl cyclase is added to, or incorporated in, metalworking fluids, paints, and stains. In a further embodiment, the modulator of bacterial adenylyl cyclase is added as an antibacterial agent to goods including, but not limited to, antibacterial soaps, shampoos, hand sanitizers, toothpaste mouthwash, disinfectants, household cleaners, paints, stains, and metalworking fluids.

In another embodiment, the modulators of bacterial adenylyl cyclase are added to growth medium to prevent or suppress bacterial growth in eukaryotic growth media. The modulator may be added to culture media for animal cell culture, for example insect and mammalian cell culture. In addition, the modulator can be added to yeast or other fungal growth media to suppress or prevent bacterial growth.

The switch to a pathogenic state by the bacteria may be monitored and measured in a number of ways. Light and electron microscopy can be used to observe morphological changes associated with the pathogenic state, such as germination. The morphology of bacterial colonies grown on agar plates containing an appropriate growth medium can be used to monitor the pathogenic state of the bacteria. Monitoring of the expression of genes that are up or down regulated upon inducing the pathogenic state can be accomplished using techniques that are well known in the art such as RT-PCR, quantitative RT-PCR, and northern blotting. The changes in specific protein levels associated with the pathogenic state can be also monitored by techniques that are well known in the art such as western blotting (immuno-blotting) or by immunoassays such as ELISA. Parameters such as appropriate growth medium and methods for measuring the pathogenic state are known by the skilled artisan.

For example, monitoring the pathogenic state in *P. aeruginosa* may be accomplished by inducing the pathogenic state and observing formation of biofilm or measuring the expression of genes or proteins associated with the pathogenic state such as TTSS proteins. Monitoring the pathogenic state in *E. coli* may be accomplished by monitoring color on MacConkey agar and monitoring the pathogenic state in *B. anthracis* may be accomplished by monitoring germination from spores.

Bacterial growth is measured by methods well known in the art. For example bacterial growth can be measured in liquid media by inoculating the appropriate media and monitoring the optical density of the media at 660 nm. The growth can also be monitored by serial dilution followed by spread plating on agar plates containing the appropriate media and counting the resulting colonies. In addition, growth of colonies on agar plates containing the appropriate media may be monitored. Growth can be measured under different parameters such as pH of the growth media, levels of $CO_2$, bicarbonate levels, and temperature.

Identifying modulators of bacterial adenylyl cyclase can be accomplished by assays that detect adenylyl cyclase activity. Detecting adenylyl cyclase activity can be accomplished in a number of ways including measuring the formation of cAMP, and measuring the conversion of ATP to cAMP. These techniques are well known in the art and commercially available kits containing detailed protocols are also an option. For example, commercial kits include the cAMP Chemiluminescent immunoassay Assay Kit, cAMP-Screen Direct™ from Applied Biosystems, cAMP Radiometric FlashPlate® ($^{125}$I) Assay Kit from PerkinElmer, the cAMP Enzyme Immunoassay Assay Kit from Sigma-Aldrich, the CatchPoint cAMP Assay Kit from Molecular Devices, and the cAMP Colorimetric Assay Kit from Calbiochem, to name a few. Many commercially available kits are intended for or adaptable to high throughput screening for adenylyl cyclase activity.

The concentration of cAMP in samples can be measured by a receptor binding assay (Nordstedt, C. and Fredholm, B B. Anal Biochem Vol 189, pp. 231-234. 1990). This method utilizes competition for binding to a cAMP binding protein (for example the regulatory subunit of mammalian protein kinase A or the CRP protein of *E. coli*) between cAMP present in the sample or standard and radiolabeled cAMP. Many different methods can be used to separate bound from free cAMP (e.g. filtration, precipitation, etc.). The amount of radiolabeled cAMP bound to the cAMP binding protein can be measured in a scintillation counter.

Another method for measuring cAMP concentration in cell extracts is by radioimmunoassay, which utilizes a cAMP-specific antibody (Steiner et al. *PNAS*. Vol. 64, pp. 367-373. 1969). A modification of this procedure utilizes a specific antibody generated against 2'-O-monosuccinyl adenosine 3',5'-cyclic monophosphate for detection of femtomolar amounts of cAMP (Harper et al. *Journal of Cyclic Nucleotide Research*. Vol. 1, pp. 207-218. 1975). By converting cAMP to an acetylated derivative that binds the antibody with higher affinity, sensitivity of these assays is enhanced. In this radioimmunoassay, a radiolabeled cAMP competes with the cAMP in the sample or standard for binding to the cAMP-specific antibody. Bound, radiolabeled cAMP is isolated and measured with a scintillation counter. Although more sensitive than the aforementioned radioreceptor method, immunoassays often require more sample manipulation, which may increase variability and assay time.

Measurements of adenylyl cyclase activity can also involve quantifying the conversion of ATP to cAMP. One method utilizes a [$^{32}$P]-labeled ATP, which is converted by the adenylyl cyclase to [$^{32}$P]cAMP. Another method involves incubating cells with [$^3$H]adenine to label intracellular pools of ATP. The [$^3$H]ATP is converted to [$^3$H]cAMP by adenylyl cyclase. Thus accumulation of [$^3$H]cAMP is used as measure of adenylyl cyclase activity. Both of these methods require the separation of radioactively labeled cAMP from other components of the reaction mixture, which is often accomplished by sequential chromatography on Dowex cation-exchange and alumina columns (Solomon et al. *Analytical Biochemistry*. Vol. 58, pp. 541-548. 1974). Another approach that can be utilized for determining adenylyl cyclase activity involves using an anti-cAMP antibody (described above) to assess cAMP formation following the incubation of cell lysates with ATP. This approach avoids the use of radioactive substrate and can also be used for assessing cAMP accumulation in intact cells. An important consideration of this assay is that only a small fraction of the ATP substrate is converted to cAMP. Thus, there is the potential that components of the reaction mixture may interfere with the antibody-cAMP interaction. For this reason, it is necessary to confirm that the buffers used for cAMP generation do not interfere with the detection of cAMP in a solution containing a known cAMP concentration.

It is important to note that adenylyl cyclase activity can be influenced by several factors depending upon the type of adenylyl cyclase (transmembrane or soluble) and the organism from which it is derived. The adenylyl cyclase activity is dependent on the presence of divalent cations, and/or dependent on the presence of other molecules such as bicarbonate, which must be present during the incubation. Also, when measuring mammalian transmembrane adenylyl cyclase, which is regulated by hormones via G-protein-coupled receptors, GTP (or a nonhydrolyzable GTP analog) should be included in the incubations. In addition, degradation of ATP by enzymes (nucleotidases and hydrolases) present in cell lysates can result in depletion of the substrate. To prevent this problem, incubations may be performed in the presence of an ATP regeneration system consisting of creatinine phosphate and creatinine phosphokinase (or phospho(enol)pyruvate and pyruvate kinase). Finally, phosphodiesterases present in cell lysates can hydrolyze cAMP to AMP. Therefore, incubations typically contain one or more phosphodiesterase inhibitors to prevent cAMP breakdown.

The conversion of ATP to cAMP in an adenylyl cyclase assay can also be determined by an immunoassay. In this assay, the antigen, cAMP, is bound to an antibody, then a second, labeled antibody is bound to the antigen-antibody complex. The amount of bound, labeled antibody is then measured. This method has several advantages relative to the conversion assay described above because it does not require the use of large amounts of $^{32}$P and the cAMP does not need to be isolated by column chromatography.

To determine the modulating activity of a compound, these assays may be performed on whole cells or cell lysates. To determine the inhibitory effects of compounds on bacterial adenylyl cyclase activity, the bacteria can be grown in conditions that elevate cAMP levels via the cyclase of interest such as elevated $CO_2$, $HCO_3^-$ or lower pH levels, with and without the compounds of interest, and analyzed for reduced cAMP levels. To determine activation of bacterial cyclases the bacteria may be grown in the presence of the compounds of interest and analyzed for increased cAMP levels. To determine inhibitory activity against human (or other subject) adenylyl cyclases, appropriate cells in culture may be grown in stimulatory conditions that increase cAMP levels. For example, stimulators of sAC include high glucose (in beta cells), neurotrophins and/or netrin (in neurons), TNF (in neutrophils), while for tmACs, stimulators include forskolin, or any of a large number of Gs-coupled hormones. The compound of interest, and assayed for reduced cAMP levels. Alternatively, inhibitory activity may be examined by observing reduction in basal levels of cyclase activity.

To determine stimulatory activity against human (or other subject) adenylyl cyclases, appropriate cells in culture may be grown in the presence of the compound and increases in cAMP levels monitored.

Alternatively these assays may be performed using purified adenylyl cyclase preparations in combination with the compound to be tested. The adenylyl cyclase to be studied can be purified by a number of ways that are known in the art for example immunoprecepitation, column chromatography with antibodies, and purification of heterologously expressed fusion proteins such as polyhistidine tagged (His-tagged) adenylyl cyclase. Polyhistidine-tags are often used for affinity purification of polyhistidine-tagged recombinant proteins that are expressed in *E. coli* or other prokaryotic expression systems. The bacterial cells are harvested by centrifugation and the resulting cell pellet can be lysed with detergents or enzymes such as lysozyme. The raw lysate is passed through a column containing immobilized nickel ions, which binds the polyhistidine tag attached to the adenylyl cyclase. The resin is then washed with phosphate buffer to remove proteins that do not specifically interact with the cobalt or nickel ion. The washing efficiency can be improved by the addition of 20 mM imidazole and proteins are then usually eluted with 150-300 mM imidazole. The purity and amount of protein can be assessed by SDS-PAGE and western blotting.

Adenylyl cyclase proteins may also by purified using immunoaffinity chromatography. The procedure involves immobilizing an antibody that specifically binds the adenylyl cyclase to a column material. A cell lysate is passed through the column, which selectively binds the protein. The protein can be eluted by changing the pH or the salt concentration.

The activity of heterologously expressed and purified bacterial adenylyl cyclase is determined by assaying in the presence of bicarbonate, $MgCl_2$ and ATP. To determine selectivity of the compound for the bacterial adenylyl cyclase, a counter screen with purified human (or other host) sAC protein can be performed. A further counter screen using a whole cell lysate stimulated with forskolin—which would reflect the activities of tmACs can also be performed.

The selectivity of a compound for a bacterial adenylyl cyclase is determined by comparing the effects of the compound on bacterial cAMP production to the effects of the compound on the subject's cAMP production. For example, a compound that is highly selective for inhibiting a bacterial adenylyl cyclase will prevent that bacterial cyclase from generating cAMP under conditions where the cyclase would, in the absence of the compound, catalyze the formation of cAMP. Further, the selective compound will not substantially inhibit or stimulate an adenylyl cyclase from the subject.

One aspect of the invention provides a method of identifying a selective modulator of bacterial adenylyl cyclase. Selectivity of the modulator of bacterial adenylyl cyclase may be determined by measuring the inhibitory or stimulatory effect on the bacterial adenylyl cyclase and by also measuring the effect on adenylyl cyclase of the intended subject. Highly selective modulators will affect the activity of the bacterial adenylyl cyclase but will have little or no effect on the activity of the adenylyl cyclase from the intended subject.

The efficacy and potential side effects of modulators of bacterial adenylyl cyclase may be tested in animal models. For example, animal models exist for acute pneumonia caused by *Pseudomonas aeruginosa* infection (Smith et al *Infection and Immunity*. Vol. 72, pp. 1677-1684), pneumonic plague caused by *Yersinia pestis*, (Lathem et al. *PNAS*. Vol 102, pp. 17786-17791), diarrhea caused by enteropathic *Escherichia coli* (Savkovic et al. *Infection and Immunity*. Vol. 73, pp. 1161-1170). Following infection, the numbers of bacteria in relevant organs can be analyzed by homogenization of the individual organs, growing serial dilutions of the homogenate on L-agar plates and counting the number of resulting colonies. Effects of infection on tissues can be examined by fixing the tissue, embedding in paraffin, and cutting sections for staining followed by microscopy. Formation of biofilms may be examined by staining these sections for the presence of capsule components, for example detecting lipopolysaccharide using antibodies to lipopolysaccharide.

Detailed descriptions of conventional methods, discussed herein such as those employed in the analysis of proteins, gene expression, light microscopy, bacterial culture, mammalian cell culture, and the like can be obtained from numerous publications such as Molecular Cloning: A Laboratory Manual (Cold Spring Harbor Laboratory Press. 1989), Current Protocols in Microbiology (Wiley InterScience), Current Protocols in Cell Biology (Wiley InterScience), and Current Protocols in Molecular Biology (Wiley InterScience). All references mentioned herein are incorporated by reference in their entirety.

EXAMPLES

Example 1

Effect of KH7 Compounds on Human Adenylyl Cyclase

Compounds were selected from the Chem Div library based on their chemical structure. These compounds were assayed to determine their effects on the activity of human soluble and transmembrane adenylyl cyclases.

In Vitro Analysis

Purified human sAC protein was used in an in vitro adenylyl cyclase assay. Purification of the protein is described in detail in Litvin et al. 2003. (J. Biol. Chem. 278:15922-15926). This paper also describes the general conditions for a sAC cyclase assay. The specific conditions for the in vitro assay are as follows.

For basal sAC activity, an assay master mixture with sufficient volume for all reactions was prepared containing:
  50 mM Tris (pH 7.5)
  20 mM Creatine phosphate
  100 U/ml creatine phosphokinase (CPK)
  1 mM DTT
  10 mM $MgCl_2$ An aliquot of the master mixture was added to the purified human sAC. The assay mixture also included the indicated concentration of KH compound, or an equivalent volume of vehicle (i.e., DMSO) as control. The reaction was started by adding 5 mM ATP (total assay volume=100 µL). The reaction mixture was incubated at 30° C. for 30 minutes and then stopped by adding 100 µl 10.2 N HCl. Stimulated assay conditions involve adding 40 mM bicarbonate and 5 mM $CaCl_2$ to the above master mixture.

Cyclic AMP levels were measured in each sample using the Correlate-EIA Direct Cyclic AMP assay kit from Assay Designs as per manufacturers instructions.

In Vivo cAMP Accumulation Assay 293T cells or 4-4 cells (hsACt stably transfected into 293T) were grown in 75 cm2 Tissue Culture Flasks until nearly confluent using DMEM (10% FBS, 1% L-Glutamine, 1% Penicillin/Streptomycin). Cells were released from the flask with 3 ml of trypsin followed by addition of 7 ml of DMEM to neutralize the trypsin. Cells were mixed by pipetting up and down with 10 ml serological pipette. To a 3 ml aliquot of the cell mixture, 6 ml of DMEM (prewarmed to 37° C.) was added followed by thorough mixing by picking up the entire 9 mls using a repeat pipettor, and slowly pipetting out against the wall of container. This was repeated this ten times to ensure the mixture in homogenous. 100 μL of cells were then added to each pre-siliconized 1.7 ml Eppindorf tubes (Costar #3207) followed by a 60 min incubation at 37° C. and 5% $CO_2$. This incubation was performed in 20-tube, round, floating racks (VWR #60986-100), which enable a quick transfer of the samples to a water bath, and the ability to mix several samples simultaneously. Following the incubation, 1 μL of the compound in DMSO was added (or just DMSO for controls). The cells were mixed before and after adding the compound, by a brief (and light) vortexing. The compounds were added while the cells were in the 37° C. water bath, followed by a 10 min incubation at 37° C. and 5% $CO_2$. Following this incubation, 1 μL it of IBMX or 1 μL of IBMX+Forskolin was added with Repeat Pipettor. The 4-4 cells receive the IBMX to a final concentration of 500 μM IBMX. The 293T cells receive IBMX and Forskolin to final concentration of 500 μM IBMX and 10 μM, respectively. Both the IBMX mix (for 4-4 cells), and the IBMX/FSK mix (for 293T cells) were 100×, and were dissolved in DMSO. Cells were mixed and incubated at 37° C. and 5% $CO_2$ for 15 min. The assay was stopped by placing the cells in an ice bath. Cells were pelleted by centrifugation at 2000×G for 7 min at 4° C. The supernatant was aspirated and 250 μL of 0.1 N HCl was added to each cell pellet followed by through vortexing for 1 min. Following a 10 min incubation at room temperature, 30 μL of each sample was added to 70 μL of 0.1 N HCl and the cAMP levels were measured using the protocol for the Direct Cyclic AMP Kit (Assay Designs, Inc. #901-066). This 30 μL plus 70 μL of 0.1 N HCl makes up the sample described in step 5 of the Assay Designs' protocol. The samples should lie in the linear range of the assay.

TABLE 1

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 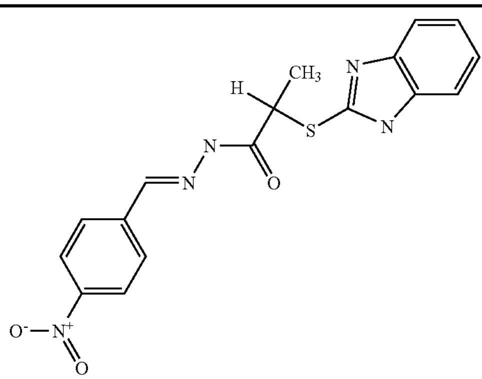 | KH7.101 | 10-100 | 50 | 10-100 | 50 | 30 | >120 |
| 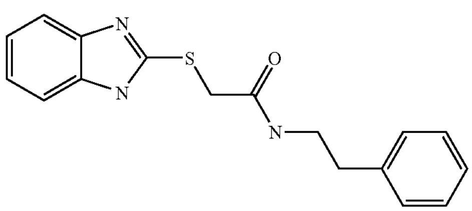 [SMILES: O=C(CSc1nc2ccccc2[nH]1)NCCc1ccccc1] | KH7.102 | >100 | 0 | >100 | 0 | 100 | >500 |
| 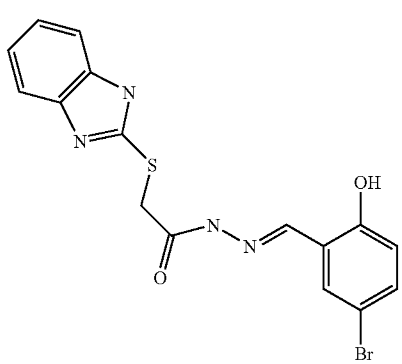 [SMILES: O=C(CSc1nc2ccccc2[nH]1)N/N=C/c1cc(Br)ccc1O] | KH7.103 | 10-100 | 100 | 10-100 | 100 | 60-120 | >120 |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| (benzimidazole-S-CH2-C(O)-NH-N=CH-C6H4-3-Br) | KH7.104 | 10-100 | 85 | 10-100 | 70 | 15 | 60-120 |
| (benzimidazole-S-CH2-C(O)-NH-N=CH-C6H3-2,4-Cl2) | KH7.105 | 10-100 | 90 | 10-100 | 90 | 15 | 60 |
| (benzimidazole-S-CH2-C(O)-NH-N=C(CH3)-C6H4-4-OCH3) | KH7.106 | 100 | 50 | 10 | 70 | 55 | >500 |
| (benzimidazole-S-CH2-C(O)-NH-N=C(CH3)-C6H4-4-Br) | KH7.107 | 10-100 | 95 | 10-100 | 95 | 60-120 | >120 |
| (benzimidazole-S-CH2-C(O)-NH-N=C(CH3)-C6H5) | KH7.108 | >100 | 0 | >100 | 0 | 30-60* may be cellular toxicity | 60-120* may be cellular toxicity |
| (benzimidazole-S-CH2-C(O)-NH-N=C(CH3)-furyl) | KH7.109 | >100 | 0 | >100 | 0 | ~120 | >120 |
| (benzimidazole-S-CH2-C(O)-NH-N=C(CH3)-C6H4-4-Cl) | KH7.110 | 10-100 | 90 | 10-100 | 90 | 30-60 | >120 |

TABLE 1-continued
| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 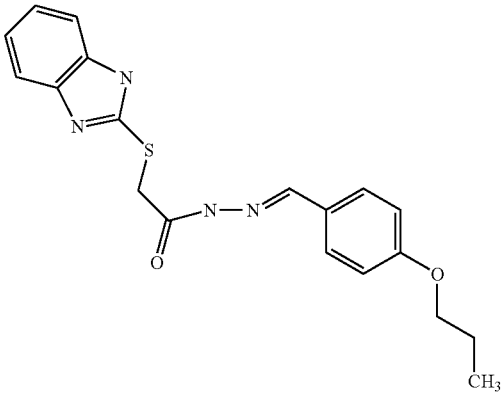 [SMILES: CCCOc1ccc(/C=N/NC(=O)CSc2nc3ccccc3[nH]2)cc1] | KH7.111 | 10-100 | 70 | 10-100 | 70 | 3-30 | 120 |
| 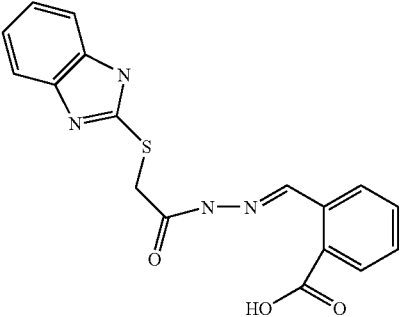 [SMILES: O=C(CSc1nc2ccccc2[nH]1)N/N=C/c1ccccc1C(=O)O] | KH7.112 | >100 | 0 | >100 | 0 | | |
| 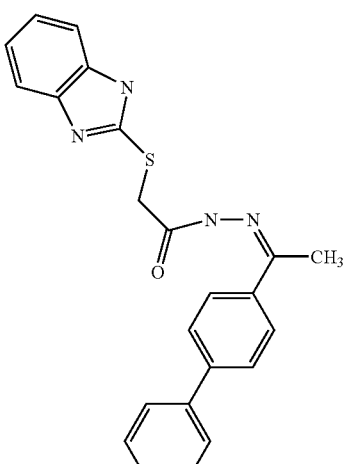 | KH7.113 | 10-100 | 80 | 10-100 | 80 | | |

TABLE 1-continued

| Structure | KH7 number | hsACt-Stim.[1] | % Inhibition (100 μM) hsACt-Basal[2] | % Inhibition (100 μM) | 4-4, Basal[3] | 293T + FSK[4] |
|---|---|---|---|---|---|---|
| | KH7.114 | >100 | 0 | >100 | 0 | 56-167 | >500 |
| | KH7.115 | 10-100 | 80 | 10-100 | 80 | | |
| | KH7.116 | 0.1-1 | Activation 50 | 0.1-1 | Activation 30 | | |
| | KH7.117 | >100 | 0 | >100 | 0 | 167-500 | >500 |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 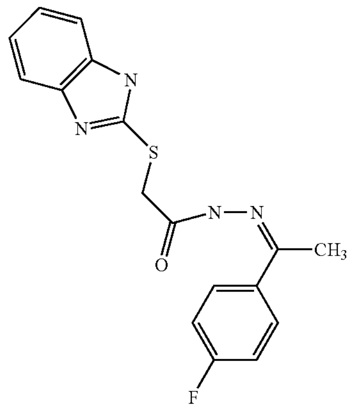 [SMILES: C/C(=N/NC(=O)CSc1nc2ccccc2[nH]1)c1ccc(F)cc1] | KH7.118 | >100 | 0 | >100 | 0 | | |
| 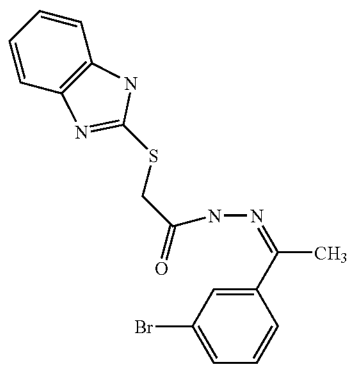 [SMILES: C/C(=N/NC(=O)CSc1nc2ccccc2[nH]1)c1cccc(Br)c1] | KH7.119 | 10-100 | 80 | 10-100 | 60 | | |
| 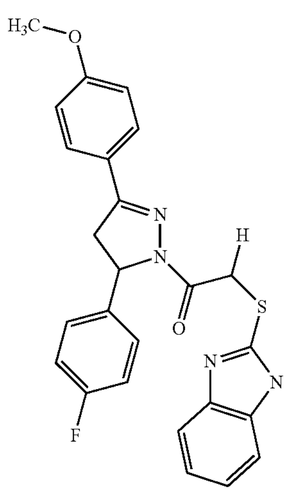 [SMILES: COc1ccc(C2=NN(C(=O)CSc3nc4ccccc4[nH]3)C(c3ccc(F)cc3)C2)cc1] | KH7.120 | 10-100 | 90 | 10-100 | 90 | | |
| 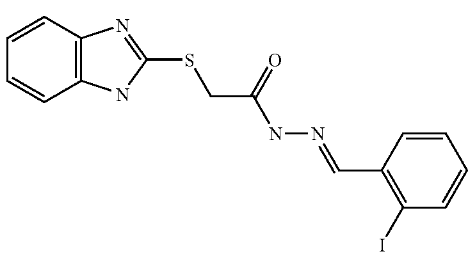 [SMILES: O=C(CSc1nc2ccccc2[nH]1)N/N=C/c1ccccc1I] | KH7.121 | 10-100 | 90 | 10-100 | 90 | | |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 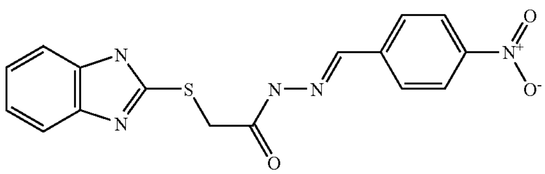 [SMILES: O=C(CSc1nc2ccccc2[nH]1)N/N=C/c1ccc([N+](=O)[O-])cc1] | KH7.122 | 100 | 50 | 100 | 50 | | |
| 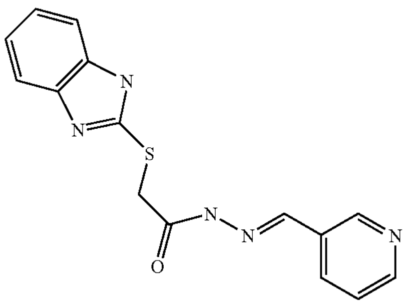 [SMILES: O=C(CSc1nc2ccccc2[nH]1)N/N=C/c1cccnc1] | KH7.123 | >100 | 0 | >100 | 0 | | |
| 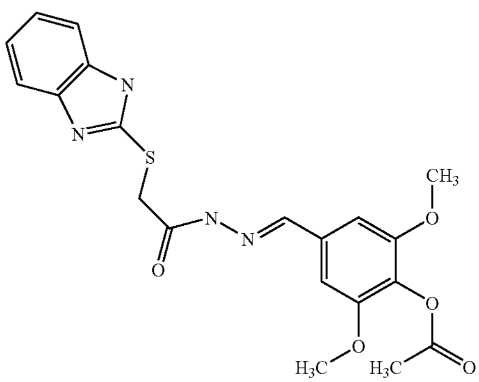 [SMILES: COc1cc(/C=N/NC(=O)CSc2nc3ccccc3[nH]2)cc(OC)c1OC(C)=O] | KH7.124 | >100 | 30 | >100 | 40 | | |
| 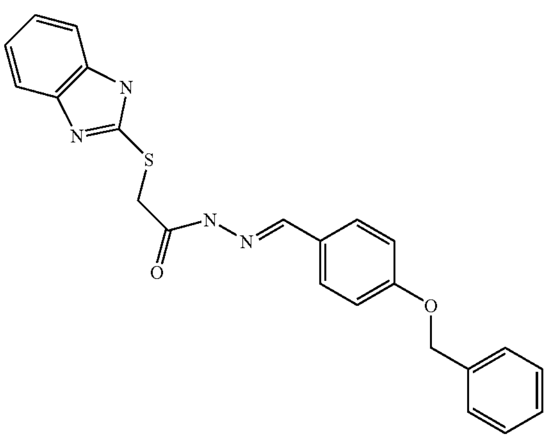 [SMILES: O=C(CSc1nc2ccccc2[nH]1)N/N=C/c1ccc(OCc2ccccc2)cc1] | KH7.125 | | | | | | |

TABLE 1-continued
| Structure | KH7 number | hsACt-Stim.[1] | % Inhibition (100 μM) hsACt-Stim.[1] | hsACt-Basal[2] | % Inhibition (100 μM) hsACt-Basal[2] | 4-4, Basal[3] | 293T + FSK[4] |
|---|---|---|---|---|---|---|---|
| 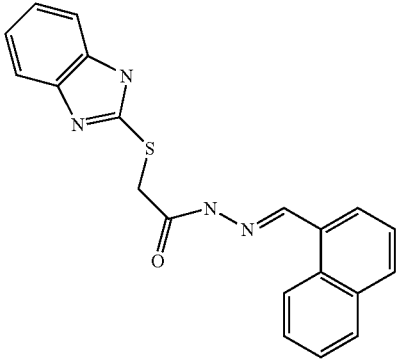 [SMILES: O=C(CSc1nc2ccccc2[nH]1)N/N=C/c1cccc2ccccc12] | KH7.126 | 10-100 | 50 | >100 | 40 | | |
| 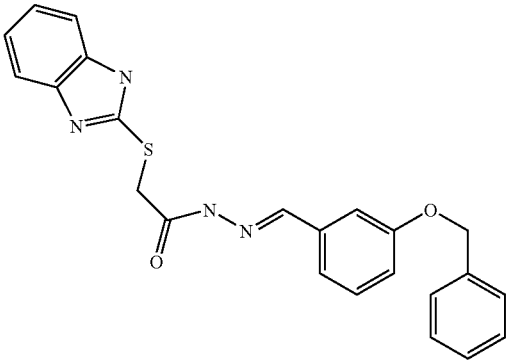 [SMILES: O=C(CSc1nc2ccccc2[nH]1)N/N=C/c1cccc(OCc2ccccc2)c1] | KH7.127 | 100 | 50 | >100 | 10 | | |
| 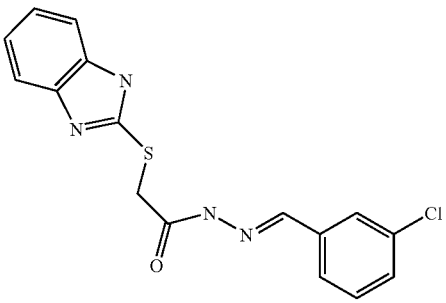 [SMILES: O=C(CSc1nc2ccccc2[nH]1)N/N=C/c1cccc(Cl)c1] | KH7.128 | 100 | 50 | 100 | 50 | | |
| 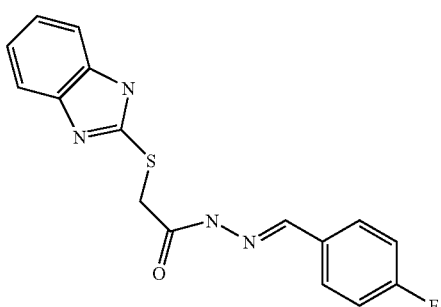 | KH7.129 | >100 | 0 | >100 | 0 | | |

TABLE 1-continued
| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 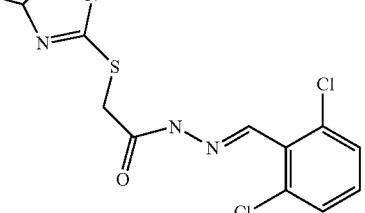 | KH7.130 | 100 | 50 | 100 | 50 | | |
| 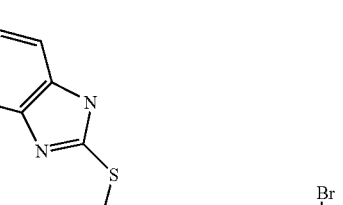 | KH7.131 | 10-100 | 60 | 10-100 | 60 | | |
| 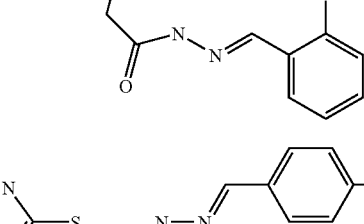 | KH7.132 | >100 | 0 | >100 | 10 | | |
| 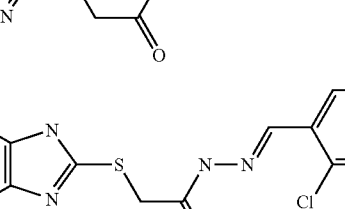 | KH7.133 | | | 10-100 | 60 | | |
| 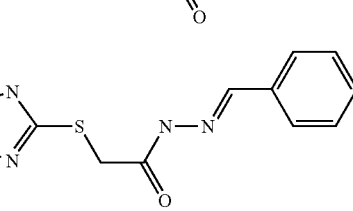 | KH7.134 | >100 | 0 | >100 | 0 | | |
| 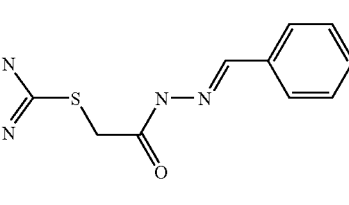 | KH7.135 | >100 | 0 | 100 | 50 | | |
| 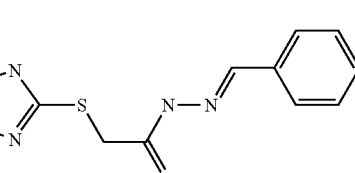 | KH7.136 | >100 | 40 | 10-100 | 80 | | |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 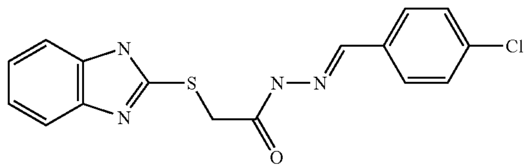 [SMILES: O=C(CSc1nc2ccccc2[nH]1)N/N=C/c1ccc(Cl)cc1] | KH7.137 | 30-100 | Activation 100 | >100 | 0 | | |
| 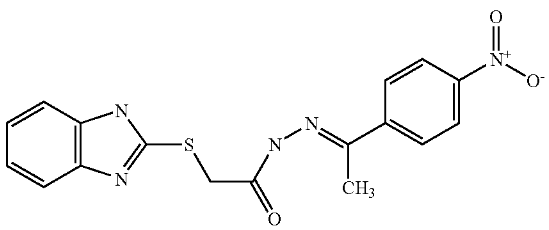 [SMILES: C/C(=N\NC(=O)CSc1nc2ccccc2[nH]1)c1ccc([N+](=O)[O-])cc1] | KH7.138 | >100 | 25 | >100 | 30 | | |
| | KH7.139 | 1.0-10 | 75 | 1.0-10 | 75 | | |
| | KH7.139 | 1.0-10 | 70 | 1.0-10 | 70 | | |
| 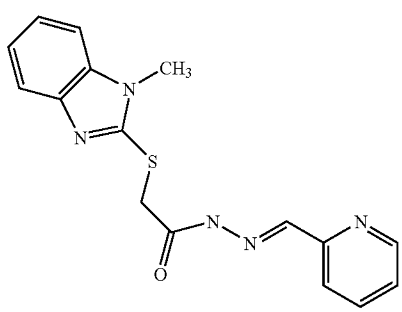 [SMILES: Cn1c(SCC(=O)N/N=C/c2ccccn2)nc2ccccc21] | KH7.140 | >100 | 0 | >100 | 0 | | |
| 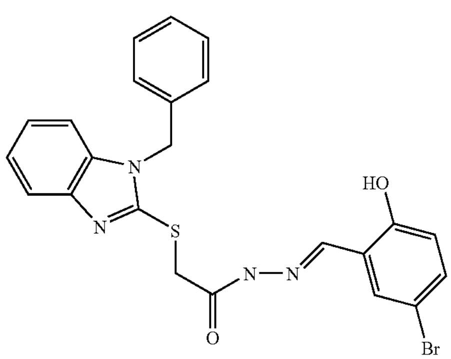 [SMILES: O=C(CSc1nc2ccccc2n1Cc1ccccc1)N/N=C/c1cc(Br)ccc1O] | KH7.141 | 1 | 80 | 1.0-10 | 80 | | |

TABLE 1-continued
| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 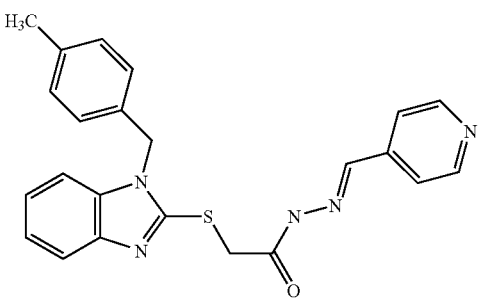 [SMILES: Cc1ccc(Cn2c(SCC(=O)N/N=C/c3ccncc3)nc3ccccc32)cc1] | KH7.142 | 1.0-10 | Activation @ 100 | >100 | 0 | | |
| 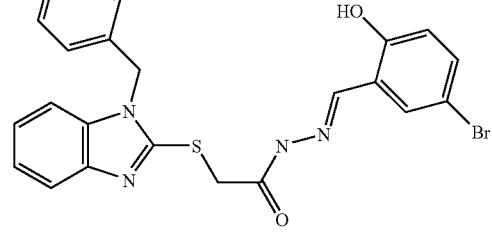 | KH7.143 | 1 | 75 | 1 | 75 | | |
| 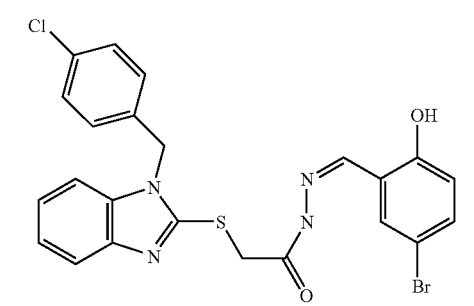 [SMILES: O=C(CSc1nc2ccccc2n1Cc1ccc(Cl)cc1)N/N=C\c1cc(Br)ccc1O] | KH7.144 | 1 | 80 | 1 | 70 | | |
| 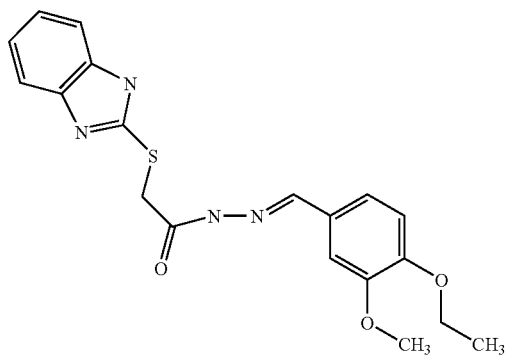 [SMILES: CCOc1ccc(/C=N/NC(=O)CSc2nc3ccccc3[nH]2)cc1OC] | KH7.145 | >100 | 20 | >100 | 0 | | |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 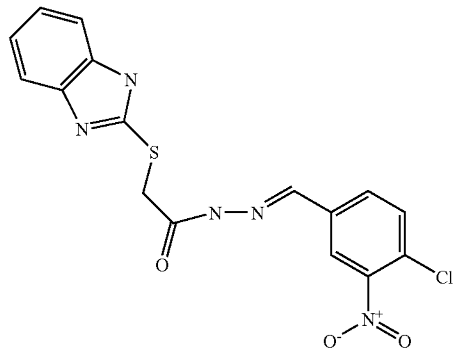 [SMILES: O=C(CSc1nc2ccccc2[nH]1)N/N=C/c1ccc(Cl)c([N+](=O)[O-])c1] | KH7.146 | >100 | 40 | 100 | 50 | | |
| 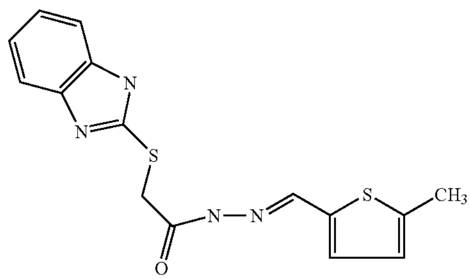 [SMILES: Cc1ccc(/C=N/NC(=O)CSc2nc3ccccc3[nH]2)s1] | KH7.147 | 10 | 60 | 10-100 | 60 | | |
| 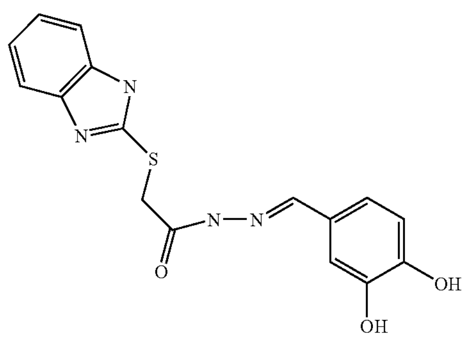 [SMILES: O=C(CSc1nc2ccccc2[nH]1)N/N=C/c1ccc(O)c(O)c1] | KH7.148 | 1.0-10 | 80 | 10-100 | 70 | | |
| 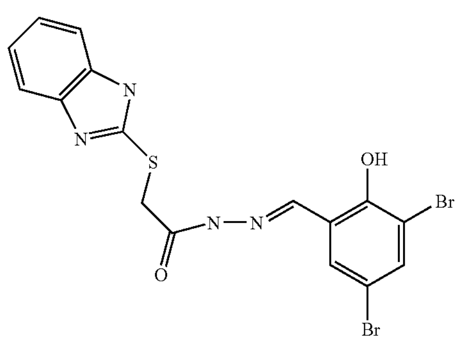 [SMILES: O=C(CSc1nc2ccccc2[nH]1)N/N=C/c1cc(Br)cc(Br)c1O] | KH7.149 | 1 | 85 | 1 | 90 | | |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 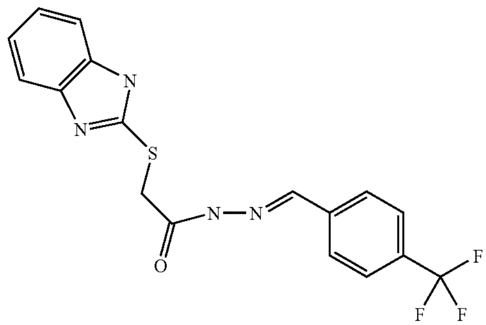 [SMILES: O=C(CSc1nc2ccccc2[nH]1)N/N=C/c1ccc(C(F)(F)F)cc1] | KH7.150 | >100 | 0 | >100 | 0 |  |  |
| 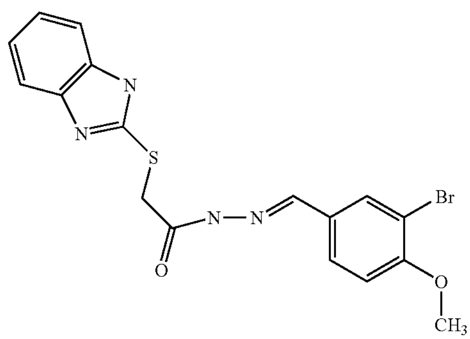 [SMILES: COc1ccc(/C=N/NC(=O)CSc2nc3ccccc3[nH]2)cc1Br] | KH7.151 | 10-100 | 50 | 10-100 | 75 |  |  |
| 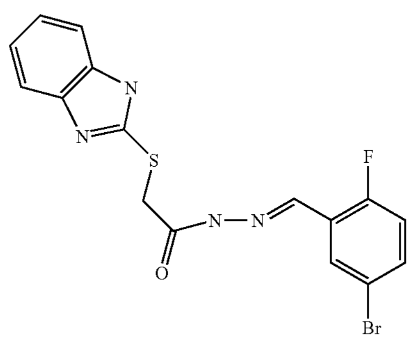 [SMILES: O=C(CSc1nc2ccccc2[nH]1)N/N=C/c1cc(Br)ccc1F] | KH7.152 |  |  | 10-100 | 60 |  |  |
| 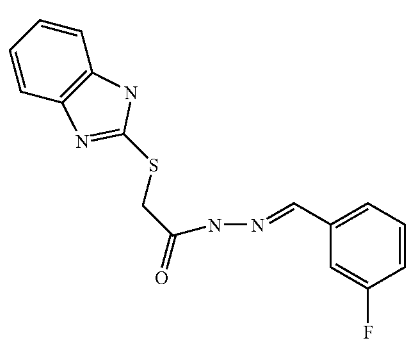 [SMILES: O=C(CSc1nc2ccccc2[nH]1)N/N=C/c1cccc(F)c1] | KH7.153 | >100 | 0 | >100 | 0 |  |  |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| (benzimidazole-S-CH2-C(O)-NH-N=CH-(2-OH-3,5-diiodophenyl)) | KH7.154 | 0.1-1 | 85 | 0.1-1 | 100 | | |
| (benzimidazole-S-CH2-C(O)-NH-N=CH-(2-Cl-5-nitrophenyl)) | KH7.155 | >100 | 0 | >100 | 0 | | |
| (benzimidazole-S-CH2-C(O)-NH-N=CH-(5-bromothiophen-2-yl)) | KH7.156 | | | | | | |
| (benzimidazole-S-CH2-C(O)-NH-N=CH-(3-methylphenyl)) | KH7.157 | | | | | | |

[1] "hsACt-Stim." is the approximate IC50 (or the dose range where the IC50 should lie) that inhibited the activity of human sAC in vitro - in this case, the stimulated activity of human sAC (i.e., calcium and bicarbonate stimulated). "% inhibition (100 μM)" is the percent that activity (the stimulated human sAC in vitro activity) was inhibited by 100 μM of compound.
[2] hsACt-Basal is the approximate IC50 (or the dose range where the IC50 should lie) that inhibited the activity of human sAC in vitro - in this case, the BASAL activity of human sAC (i.e., just Mg-ATP as substrate, with no calcium or bicarbonate added). "% inhibition (100 μM)" is the percent that activity (the BASAL human sAC in vitro activity) was inhibited by 100 μM of compound.
[3] 4-4, basal is activity in a cellular assay - it is the approximate IC50 (or the dose range where the IC50 should lie) that inhibited the activity of a stable cell line overexpressing human sAC - basically, this is a good indication of in vivo efficacy against human sAC
[4] 293T + FSK is also a celllular assay, but in this case, the activity that is being measured is due to endogenous transmembrane adenylyl cyclases. This is an indication of the selectivity of these compounds versus the other forms of adenylyl cyclase in humans.

Example 2

Pseudomonas Adenylyl Cyclase Assay

*P. aeruginosa* CyaB (a Class III adenylyl cyclase) was heterologously expressed in *E. coli* as a HIS-tagged, fusion protein. Expression of the fusion protein was induced by Isopropyl β-D-1-thiogalactopyranoside (IPTG) t at 21° C. (empirically found to be best temperature for expression). The His-CyaB fusion protein was purified using a nickel affinity column according to standard protocols in the absence of any reducing agent. Eluted protein was dialyzed into storage buffer consisting of: 50 mM Tris (pH 8.5), 10 mM NaCl, 2 mM MgCl$_2$, and 25% glycerol.

The purified CyaB was assayed for cyclase activity as follows. An assay master mixture with sufficient volume for all reactions was prepared containing:

50 mM Tris (pH 8.5)
20 mM Creatine phosphate
100 U/ml creatine phosphokinase (CPK)
1 mM DTT
15 mM MgCl$_2$ An aliquot of the master mixture was added to the purified CyaB. The assay mixture also included the indicated concentration of KH compound, or an equivalent volume of vehicle (i.e., DMSO) as control. The reaction was started by adding 1 mM ATP (total assay volume=100 μL). The reaction mixture was incubated at 40° C. for 30 minutes and then stopped by adding 100 μl 0.2 N HCl.

Cyclic AMP levels were measured in each sample using the Correlate-EIA Direct Cyclic AMP assay kit from Assay Designs as per manufacturers instructions.

Figure 2:
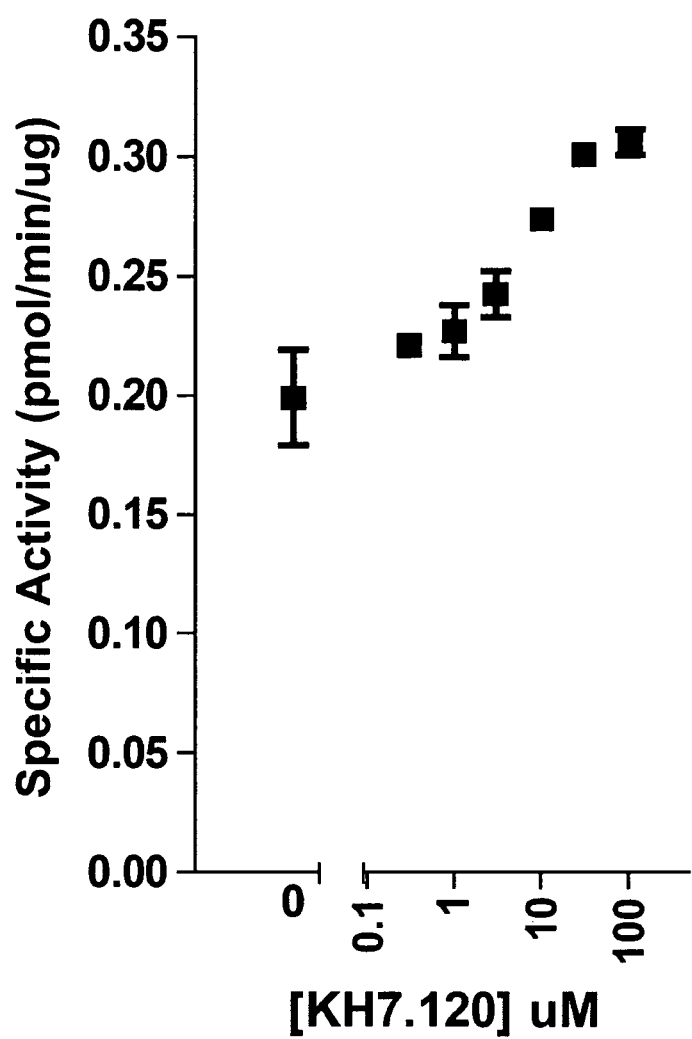

By this assay, the compound KH7.148 was determined to be an inhibitor of the CyaB adenylyl cyclase from *P. aeruginosa* (see FIG. 1) and KH7.120 was determined to be an activator of CyaB adenylyl cyclase (see FIG. 2).

We claim:

1. A method for the treatment of a subject with a disease caused by infection by bacteria, the method comprising: administering to a subject a therapeutic amount of a modulator of a bacterial adenylyl cyclase of the infecting bacteria, wherein the modulator interacts with the bacterial adenylyl cyclase, and wherein the modulator of bacterial adenylyl cyclase is selected from the group consisting of:

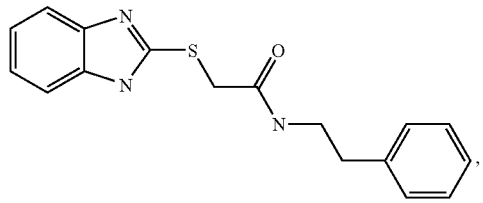

KH7.102

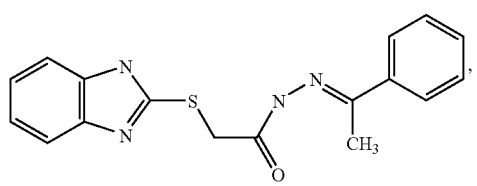

KH7.108

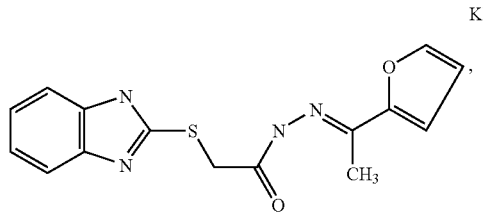

KH7.109

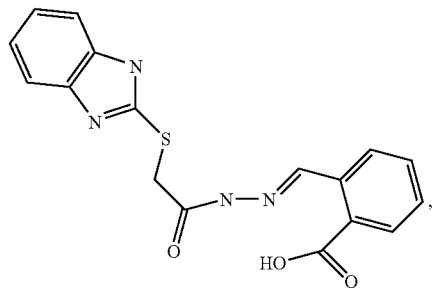

KH7.112

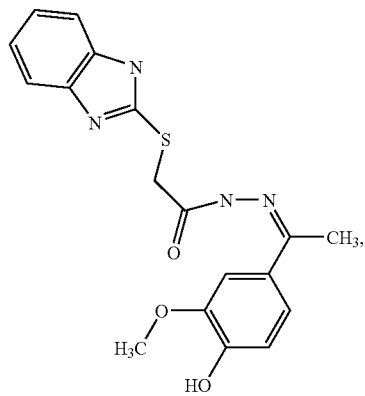

KH7.114

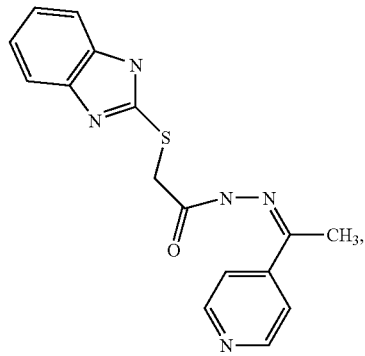

KH7.117

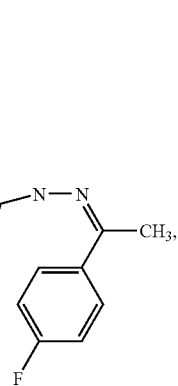

KH7.118

KH7.123
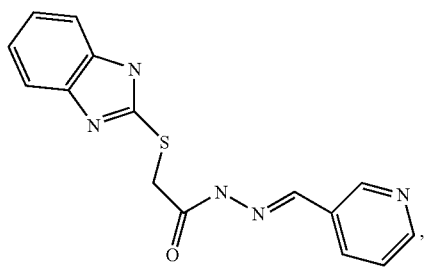

KH7.129
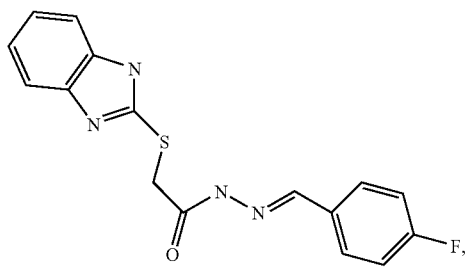

KH7.132
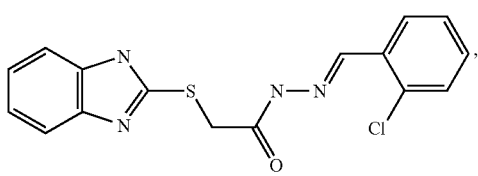

KH7.133
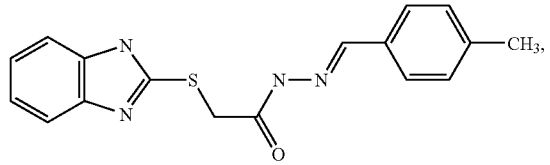

KH7.134
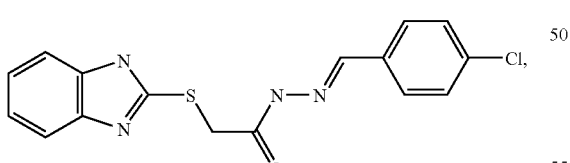

KH7.137

KH7.140
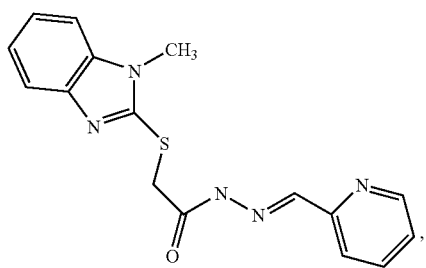

KH7.150
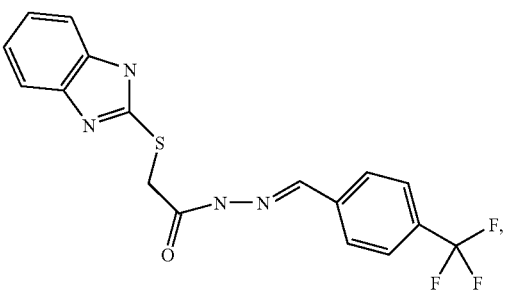

KH7.151
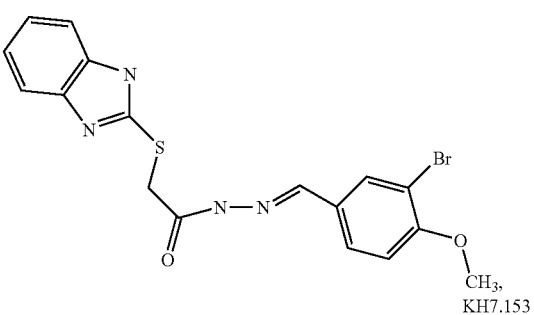

KH7.153

KH7.155 and combinations thereof, or wherein the modulator of bacterial adenylyl cyclase is selected from catechol estrogens and derivatives thereof.

2. The method of claim 1, wherein the bacterial adenylyl cyclase is selected from the group consisting of Class I, Class III, and Class IV adenylyl cyclases, and wherein the modulator of bacterial adenylyl cyclase is selective relative to adenylyl cyclases of the subject.

3. The method of claim 1, wherein the amount of modulator of bacterial adenylyl cyclase administered is effective at substantially preventing the bacteria from changing to a pathogenic state from a non-pathogenic state, or wherein the amount of the modulator of bacterial adenylyl cyclase administered causes the bacteria to substantially revert to a non-pathogenic state from a pathogenic state.

4. The method of claim 3, wherein the modulator of the bacterial adenylyl cyclase substantially prevents the infecting bacteria from changing shape.

5. The method of claim 3, wherein the modulator of the bacterial adenylyl cyclase substantially prevents the infecting bacteria from producing toxins.

6. The method of claim 3, wherein the modulator of the bacterial adenylyl cyclase substantially prevents the infecting bacteria from forming biofilms.

7. The method of claim 3, wherein the modulator of the bacterial adenylyl cyclase substantially prevents the infecting bacteria from increasing or decreasing growth rate.

8. The method of claim 1, wherein the modulator of the bacterial adenylyl cyclase inhibits the bacterial adenylyl cyclase.

9. The method of claim 1, wherein the modulator of the bacterial adenylyl cyclase activates the bacterial adenylyl cyclase.

10. The method of claim 1, wherein the modulator of the bacterial adenylyl cyclase has a substantially bactericidal effect upon the infecting bacteria.

11. The method of claim 1, wherein the modulator of the bacterial adenylyl cyclase has a substantially bacteriostatic effect upon the infecting bacteria.

12. The method of claim 1, wherein the amount of modulator of bacterial adenylyl cyclase administered does not inhibit or prevent growth of the bacteria.

13. The method of claim 1, wherein the amount of modulator of bacterial adenylyl cyclase administered does not kill the bacteria.

14. The method of claim 1, wherein the modulator of the bacterial adenylyl cyclase affects more than one bacterial adenylyl cyclase of one infecting bacteria.

15. The method of claim 1, wherein the modulator of the bacterial adenylyl cyclase affects more than one bacterial adenylyl cyclase of more than one infecting bacteria.

16. The method of claim 1, wherein the amount of modulator of bacterial adenylyl cyclase administered does not affect whether the bacteria enters a pathogenic state.

17. The method of claim 1, wherein the bacterial adenylyl cyclase is $CO_2/HCO_3/pH$ sensitive.

18. The method of claim 17, wherein the modulator affects the response of the infecting bacterial adenylyl cyclase to $CO_2$.

19. The method of claim 17, wherein the modulator affects the response of the infecting bacterial adenylyl cyclase to $HCO_3$.

20. The method of claim 17, wherein the modulator affects the response of the infecting bacterial adenylyl cyclase to pH.

21. The method of claim 1, wherein the infection is caused by bacteria selected from the group consisting of Gram negative bacteria, Gram negative cocci, Gram negative rods, Gram positive bacteria, Gram positive cocci, and Gram positive rods.

22. The method of claim 1, wherein the infection by bacteria is caused by a spirochete.

23. The method of claim 1, wherein the infection by bacteria is caused by enteric bacteria.

24. The method of claim 23, wherein the infection is caused by an enteric bacteria selected from the group consisting of *Escherichia coli, Salmonella enterica, Shigella, Shigella dysenteriae, Vibrio cholerae, Vibrio vulnificus, Vibrio parahaemolyticus, Virio vulnificus, Campylobacter jejuni, Klebsiella, Enterobacter, Serratia, Proteus, Providencia*, and *Morganella*.

25. The method of claim 1, wherein the infection is caused by a bacteria selected from the group consisting of *Bacillus anthracis, Bacillus cereus, Clostridium tetani, Clostrium botulinum, Clostridium perfringens, Clostridium difficile, Mycobacterium tuberculosis Legionella pneumophilla, Vibrio cholera, Staphylococcus aureus, Staphylococcus epidermidis, Staphylococcus saprophyticus, Streptococcus pyogenes, Streptococcus agalactiae, Enterococcus faecalis, Streptococcus bovis, Streptococcus pneumoniae, Streptococcus viridans, Pseudomonas aeruginosa, Corynebacterium diphtheriae, Listeria monocytogenes, Burcella, Francisella tularensis, Yersinia enterocolitica, Yersinia pseudotuberculosis, Yersinia pestis, Pasteurella multocida, Mycobacterium tuberculosis, Mycobacterium bovis, Mycobacterium avium, Mycobacterium leprae, Actinomyces israelii, Nocardia asteroides, Mycoplasma pneumoniae, Treponema pallidum, Borrelia brugdorferi, Borrelia afzelii, Borrelia garinii, Leptospira interrogans, Chlamydia psittaci, Chlamydia trachomatis, Chlamydia pneumoniae, Rickettsia rickettsii, Coxiella burnetii, R. Prowazekii, Gardnerella vaginalis, Lactobacillus, Peptococcus, Peptostreptococcus, Propionibacterium, Tropheryma, Burkholderia pseudomallei*, and *Burkholderia mallei*.

26. The method of claim 1, wherein the infection is caused by *Pseudomonas aeruginosa*.

27. The method of claim 1, wherein the infection is caused by bacteria that are resistant to one or more antibacterial agents.

28. The method of claim 1, wherein the subject is a eukaryote.

29. The method of claim 1, wherein the subject is a plant.

30. The method of claim 1, wherein the subject is an animal.

31. The method of claim 1, wherein the subject is a bird.

32. The method of claim 31, wherein the bird is poultry.

33. The method of claim 1, wherein the subject is a fish.

34. The method of claim 1, wherein the subject is a mammal.

35. The method of claim 34, wherein the mammal is livestock or pet.

36. The method of claim 35 wherein the livestock animal is selected form the group consisting of cattle, swine, and sheep.

37. The method of claim 35 wherein the pet is selected form the group consisting of dogs, cats and horses.

38. The method of claim 34, wherein the mammal is a human.

39. The method of claim 38, wherein the human is immune compromised.

40. The method of claim 39, wherein the immune compromised human is selected from the group consisting of a human infected with HIV, a human undergoing chemotherapy, a human affected by a blood cancer, a human transplant recipient, a human receiving immunosuppressant medication, a human receiving an opioid medication, and a human burn victim.

41. The method of claim 38, wherein the human has an opportunistic lung infection.

42. The method of claim 41, wherein the human is selected from the group consisting of a human who has asthma, a human who has cystic fibrosis, a human who has sarcoidosis.

43. The method of claim 38, wherein the human has been exposed to airborne infectious agents.

44. The method of claim 43, wherein the human is selected from the group consisting a human who has tuberculosis and a human with anthrax infection.

45. The method of claim 1, wherein the modulator of bacterial adenylyl cyclase does not inhibit adenylyl cyclases of the subject.

46. The method of claim 1, wherein the modulator of bacterial adenylyl cyclase is sufficiently selective against adenylyl cyclases of the subject that a therapeutic effect upon the infecting bacteria can be achieved without toxic regulation of subject's adenylyl cyclase occurring.

47. The method of claim 1, wherein the modulator of bacterial adenylyl cyclase is selected from the group consisting of small molecules, aptamers, and interfering RNA.

48. The method of claim 1, wherein the modulator of bacterial adenylyl cyclase is selected from the group consisting of:

KH7.102

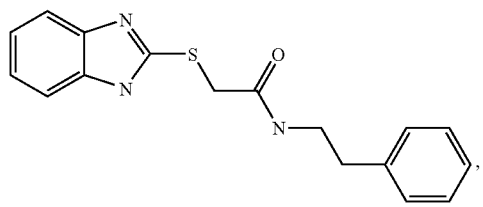

KH7.108

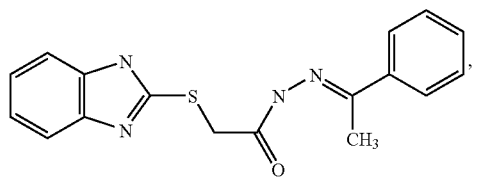

KH7.109

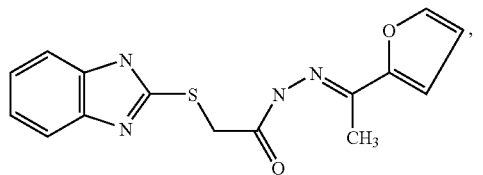

KH7.112

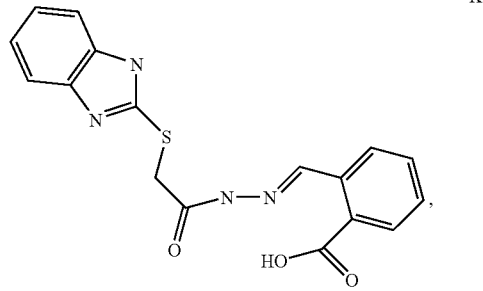

KH7.114

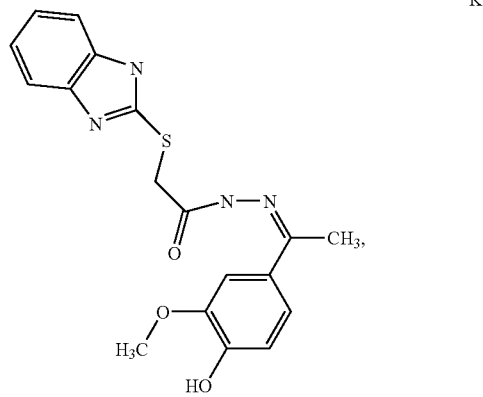

KH7.117

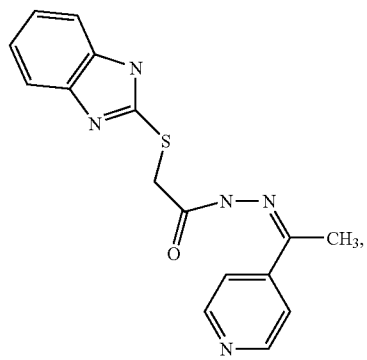

KH7.118

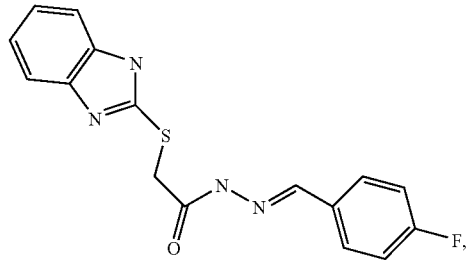

KH7.123

KH7.129

KH7.132

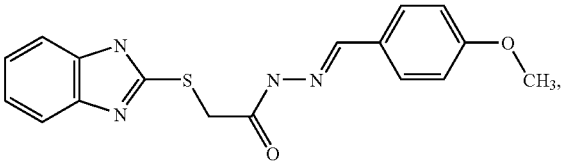

-continued

KH7.133
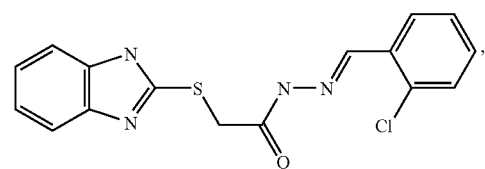

KH7.134
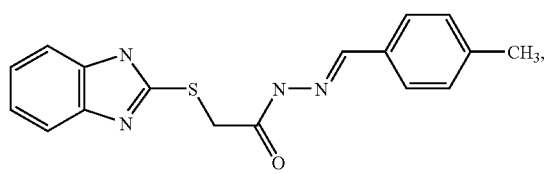

KH7.137
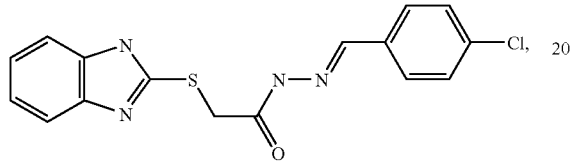

KH7.140
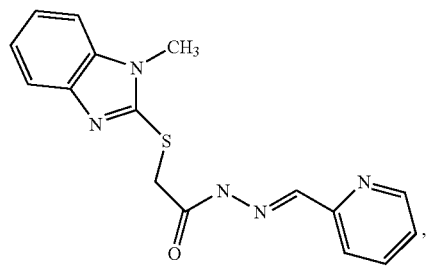

KH7.150
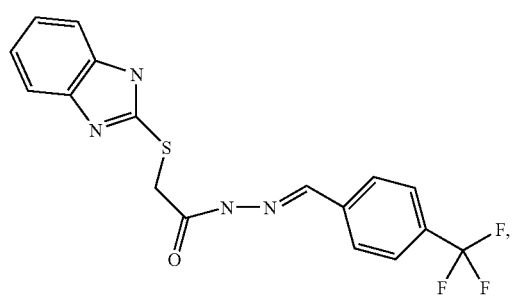

-continued

KH7.151

KH7.153

, and

KH7.155 and combinations thereof.

49. The method of claim 1, wherein the modulator of bacterial adenylyl cyclase is selected from catechol estrogens and derivatives thereof.

50. The method of claim 1, further comprising administration of one or more additional therapeutic agents.

51. The method of claim 50, wherein the additional therapeutic agent is an antibacterial agent.

* * * * *